(12) United States Patent
Cropp et al.

(10) Patent No.: US 8,883,453 B2
(45) Date of Patent: Nov. 11, 2014

(54) CODON SPECIFIC MUTAGENESIS

(75) Inventors: Thomas Ashton Cropp, Bethesda, MD (US); Kelly Anne Daggett, Beltsville, MD (US)

(73) Assignee: University of Maryland, College Park, MD (US)

( * ) Notice: Subject to any disclaimer, the term of this patent is extended or adjusted under 35 U.S.C. 154(b) by 1578 days.

(21) Appl. No.: 12/112,706

(22) Filed: Apr. 30, 2008

(65) Prior Publication Data
US 2009/0004702 A1 Jan. 1, 2009

Related U.S. Application Data

(60) Provisional application No. 60/914,793, filed on Apr. 30, 2007.

(51) Int. Cl.
*C12N 15/64* (2006.01)
*C12P 19/34* (2006.01)
*C12N 15/10* (2006.01)

(52) U.S. Cl.
CPC .................................. *C12N 15/102* (2013.01)
USPC ......................... 435/91.2; 435/440; 435/91.4

(58) Field of Classification Search
None
See application file for complete search history.

(56) References Cited

U.S. PATENT DOCUMENTS

| 5,919,694 | A | * | 7/1999 | Sugimoto et al. | ........ 435/252.33 |
| 6,420,524 | B1 | | 7/2002 | Craig | |
| 7,741,128 | B2 | * | 6/2010 | Su | ................................ 436/501 |
| 2003/0143578 | A1 | * | 7/2003 | Pruitt et al. | ........................ 435/6 |
| 2006/0019301 | A1 | * | 1/2006 | Hansen et al. | ..................... 435/6 |

OTHER PUBLICATIONS

Jones D. Dafydd, "Triplet nucleotide removal at random positions in a target gene: the tolerance of TEM-1 β-lactamase to an amino acid deletion", School of Biosciences, Biomedical Sciences Building, Cardiff University, Cardiff CF10 3US, UK, Nucleic Acids Research, 2005, vol. 33, No. 9, pp. 16-23.
Finnzymes Tools for Molecular Biology; "Mutation Generation System™ KIT (MGS™ Kit)" pp. 1. <http://www.finnzymes.com/sequencing_mutagenesis . . . > visited Apr. 2007.
New England Biolabs Inc.; "GPS™-LS Linker Scanning System" pp. 1-3. <http://www.neb.com/nebecomm/products/productE7102.asp> visited Apr. 2, 2007.

* cited by examiner

*Primary Examiner* — Catherine Hibbert
(74) *Attorney, Agent, or Firm* — Arent Fox LLP

(57) ABSTRACT

Materials and methods are provided for replacing one or more amino acids in a polypeptide with an amino acid of choice to form mutant proteins. Both naturally and non-naturally occurring amino acids can be inserted. A population of mutant proteins can be created in which an amino acid residue has replaced an existing residue at random locations along the primary sequence of the protein. The provided techniques allow for the study of proteins and development of proteins with improved functionalities.

23 Claims, 11 Drawing Sheets

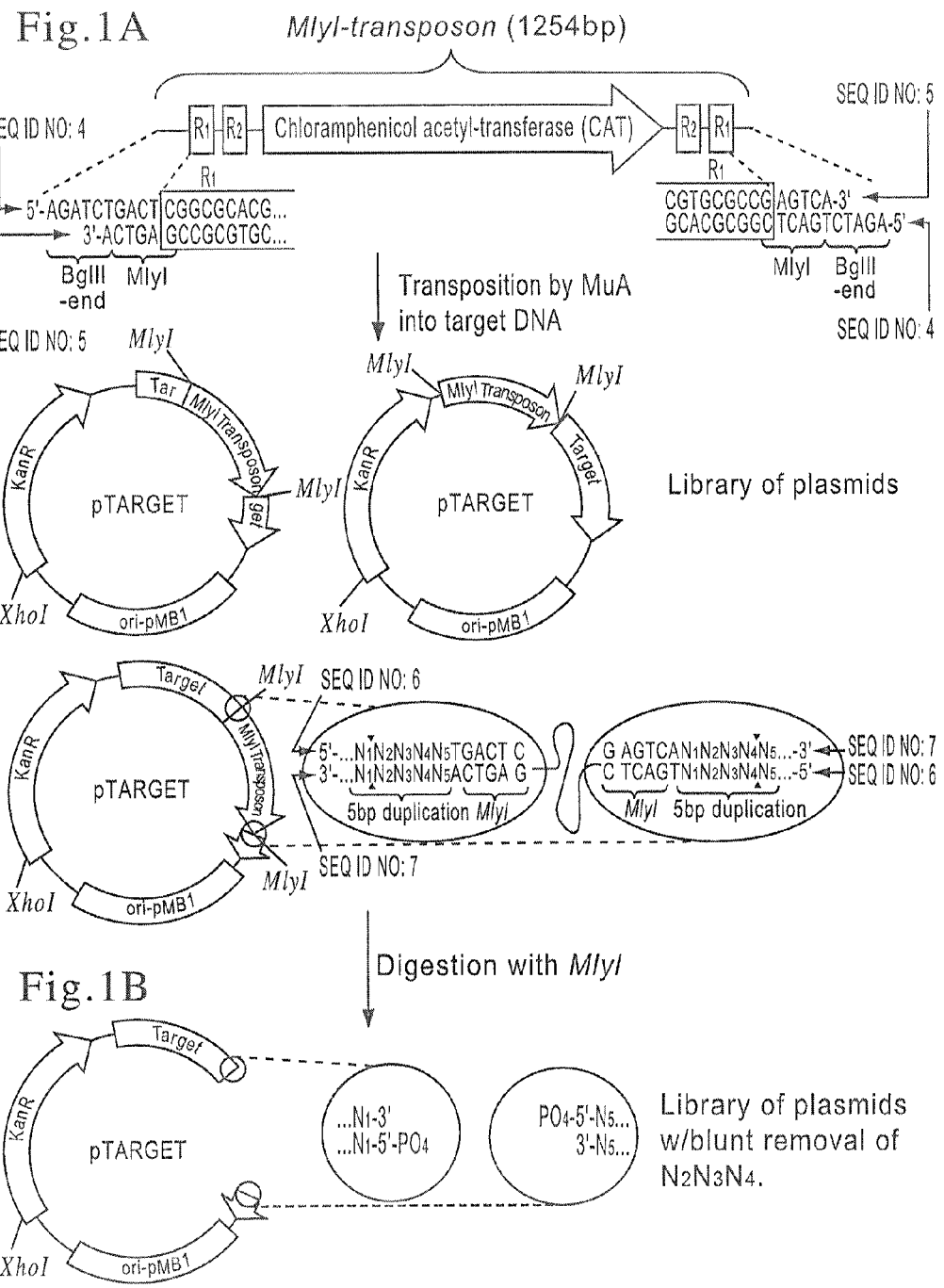

CODON SPECIFIC MUTAGENESIS

This application claims priority to U.S. Provisional Patent Application No. 60/914,793, filed Apr. 30, 2007.

SEQUENCE LISTING

The instant application contains a Sequence Listing which has been submitted in ASCII format via EFS-Web and is hereby incorporated by reference in its entirety. Said ASCII copy, created on Jun. 24, 2011, is named 18172132.txt and is 25,131 bytes in size.

BACKGROUND OF THE INVENTION

The development of oligonucleotide-directed mutagenesis is perhaps the most influential tool in the study of protein structure and function. Existing methods include "Quikchange" mutagenesis, the Kunkel method, and enzymatic inverse PCR. As they are all based on annealing synthetic DNA, every desired mutant construction involves a pair of mutagenic oligonucleotides, a thermocycling reaction, and subsequent cloning and sequence verification of the mutated genes. This places both manpower and financial limitations on high-throughput mutagenesis studies such as alanine scanning and directed evolution. Practicality dictates that it is nearly impossible to efficiently make every alanine, or other amino acid, mutation of a 500 amino acid protein using current methods. Accordingly, there is a need for new mutagenic techniques that offer greater efficiency and control.

SUMMARY OF THE INVENTION

The invention provides methods and materials for generating codon specific mutations in proteins, wherein the replacement codon is chosen and controlled by the user, although the insertion location can be random. These methods are also referred to as "codon scanning mutagenesis." Because the goal in codon scanning mutagenesis is to probe a protein at multiple codon positions, a plasmid referred to can be a member of a population of mutant plasmids.

A method of codon specific mutagenesis is provided according to one aspect of the invention. The method comprises the following steps: A plasmid is provided comprising a target open reading frame, a selectable marker, and an origin of replication. A linear transposon fragment is provided comprising a double stranded nucleic acid with first and second ends, a second selectable marker, and two restriction sites, unique to the original plasmid, and located less than 10 base pairs from the 5' and 3' ends of the transposon fragment. The transposon fragment and the first plasmid are reacted in the presence of the cognate transposase enzyme to cause integration of the transposon into the plasmid at random insertion sites, and duplication of N nucleotides, depending on the transposase used. The second plasmid is digested with the restriction enzyme corresponding to the unique site. A collection of randomly linearized plasmids is generated. This collection of plasmids is ligated with a linear double-stranded nucleic acid comprising a second selectable marker capable of selecting correct in-frame ligation events, and additional unique TypeII S restriction sites positioned such that digestion removes N+3 nucleotides from the mixture of plasmids, and leaves three new nucleotides in their place to yield a plasmid that encodes a mutant polypeptide.

A method of codon specific mutagenesis is provided in accordance with an aspect of the invention. The method comprises the following steps: A plasmid is provided that comprises a target open reading frame, a selectable marker capable of selecting correct in-frame ligation events, and an origin of replication. A linear transposon fragment is provided comprising a double stranded nucleic acid with first and second ends, a second selectable marker and two unique primer binding sites that differ by greater than 5 degree Tm. The transposon and the first plasmid are reacted in the presence of the cognate transposase enzyme to cause integration of the transposon into the plasmid at random insertion sites, and duplication of N nucleotides, depending on the transposase used. The two primer binding sites are used for inverse PCR with two oligonucleotides that incorporate unique TypeII S restriction sites positioned such that digestions removes N+3 nucleotides the mixture of plasmids, and leaves three new nucleotides in their place.

A method of codon specific mutagenesis is provided in accordance with an aspect of the invention. The method comprises the following steps: A first plasmid is provided comprising a target open reading frame, a first selectable marker, and an origin of replication, wherein the first plasmid does not contain a MlyI restriction site. A linear Mu transposon is provided comprising a double stranded nucleic acid with first and second ends, a second selectable marker, a first MlyI restriction site proximal the first end and a second MlyI restriction site proximal the second end, wherein the first and second ends comprise overhanging DNA sequence (sticky ends). The Mu transposon and the first plasmid are reacted in the presence of MuA transposase to cause integration of the Mu transposon into the plasmid at an insertion site with accompanying removal of the sticky ends and duplication of a five base pair sequence of the first plasmid at the insertion site to form a second plasmid. The second plasmid is digested with MlyI restriction enzyme to form a first linear blunt-ended double-stranded nucleic acid, wherein the nucleic acid comprises the first selectable marker. A codon scar linker comprising a second linear blunt-ended double-stranded nucleic acid with first and second ends, a first MlyI restriction site proximal the first end and a second MlyI restriction site proximal the second end, wherein the first or second end comprises a mutant replacement codon, and wherein the codon scar linker comprises a third selectable marker. The first linear blunt-ended double-stranded nucleic acid is ligated with the codon scar linker to form a third plasmid. The third plasmid with MlyI restriction enzyme to form a third linear blunt-ended double-stranded nucleic acid comprising the mutant replacement codon and first and second ends. The first and second ends of the third linear blunt-ended double-stranded nucleic acid comprising the mutant replacement codon are intramolecularly ligated to form a fourth plasmid, wherein the fourth plasmid encodes a mutant polypeptide.

A method of codon specific mutagenesis is provided in accordance with an aspect of the invention. The method comprises the following steps: A first plasmid is provided comprising a target open reading frame, a first selectable marker, and an origin of replication, wherein the first plasmid does not contain a BsgI restriction site. A linear Mu transposon is provided comprising a double stranded nucleic acid with first and second ends, second and third selectable markers, a mutant codon proximal the first end, wherein the first and second ends comprise overhanging DNA sequence, and wherein at least the second selectable marker is in the same translational reading frame as the mutant codon. The Mu transposon and first plasmid are reacted in the presence of MuA transposase to cause integration of the Mu transposon into the plasmid at an insertion site with accompanying removal of the sticky ends and duplication of a five base pair sequence of first plasmid at the insertion site to form a second plasmid. An inverse-polymerase chain reaction (inverse-PCR) is performed employing the second plasmid as a template and first and second oligonucleotide primers, wherein each primer comprises an overhanging nucleic acid sequence and a template binding sequence, wherein the overhanging nucleic acid sequence comprises a BsgI restriction site, wherein the inverse PCR produces a second linear double-stranded nucleic acid. The second linear double-stranded nucleic acid is digested with BsgI restriction enzyme to form a third linear double-stranded nucleic acid, wherein the third double-stranded nucleic acid comprises the mutant replacement codon, the first selectable marker, and first and second ends with overhanging nucleic acid sequence. The third double-stranded nucleic acid is repaired with PHUSION™ polymerase or other suitable proofreading polymerase to form a fourth double-stranded nucleic acid with blunt ends. The fourth double-stranded nucleic acid sequence is intramolecularly ligated to form a third plasmid, wherein the third plasmid encodes a mutant polypeptide.

A method of codon specific mutagenesis is provided in accordance with an aspect of the invention. The method comprises the following steps: A first plasmid is provided comprising a target open reading frame, a first selectable marker, and an origin of replication, wherein the first plasmid does not contain a NotI restriction site. A linear Mu transposon is provided comprising a first double-stranded nucleic acid with first and second ends, a second selectable marker, a first NotI restriction site proximal the first end and a second NotI restriction site proximal the second end, wherein the first and second ends comprise overhanging (sticky-ended) DNA sequence. The Mu transposon and first plasmid are reacted in the presence of MuA transposase to cause integration of the Mu transposon into the plasmid at an insertion site with accompanying removal of the sticky ends and duplication of a five base pair sequence of the first plasmid at the insertion site to form a second plasmid. The second plasmid is digested with NotI restriction enzyme to form a second linear sticky-ended double-stranded nucleic acid, wherein the nucleic acid comprises the first selectable marker. A codon scar linker is provided comprising a third linear double-stranded nucleic acid with first and second ends, a first NotI restriction site proximal the first end, a second NotI restriction site proximal the second end, a mutant replacement codon between the first and second NotI restriction sites, a single BsgI restriction site located adjacent to the first NotI restriction site and between the first NotI restriction site and the mutant replacement codon, a single MlyI restriction site located between the BsgI and the mutant replacement codon, and a single BsaXI restriction site located adjacent to the second NotI site and between the mutant replacement codon and the second NotI restriction site and wherein the codon scar linker comprises a third selectable marker, and wherein the codon scar linker has been digested with NotI restriction enzyme to provide sticky ends. The second linear sticky-ended double-stranded nucleic acid is ligated with the codon scar linker to form a third plasmid. The third plasmid is digested with BsgI and MlyI restriction enzymes to form a fourth linear sticky-ended double-stranded nucleic acid comprising the mutant replacement codon. The sticky ends of the second linearized sticky-ended double-stranded nucleic acid are blunted to form a first linear blunt-ended double-stranded nucleic acid. The first and second ends of the first linear blunt-ended double-stranded nucleic acid comprising the mutant replacement codon and first and second ends are ligated intramolecularly to form a fourth plasmid. The fourth plasmid is digested with BsaXI restriction enzyme to form a fifth linear sticky-ended double-stranded nucleic acid comprising the mutant replacement codon. The sticky ends of the fifth linear sticky-ended double-stranded nucleic acid are blunted to form a second linearized blunt-ended double-stranded nucleic acid with first and second ends. The first and second ends of the second linear blunt-ended double-stranded nucleic acid comprising the mutant replacement codon are ligated intramolecularly to form a fifth plasmid, wherein the fifth plasmid encodes a mutant polypeptide.

Nucleic acid constructs employed in the methods of the invention are also part of the invention. Kits including one or more material of the invention are provided that can be used to carry out the methods of the invention in whole or part. Method of transforming organisms with the plasmids of the present invention and methods of expressing mutant proteins from the same are also included.

In the methods, materials, and kits of the invention, substitution of restriction enzyme, transposon, and other components can be carried out without departing from the scope of the invention.

BRIEF DESCRIPTION OF THE DRAWINGS

FIGS. 1A-1C show stages of codon specific mutagenesis in accordance with the invention.

DETAILED DESCRIPTION OF THE PREFERRED EMBODIMENTS

Figure 1C:
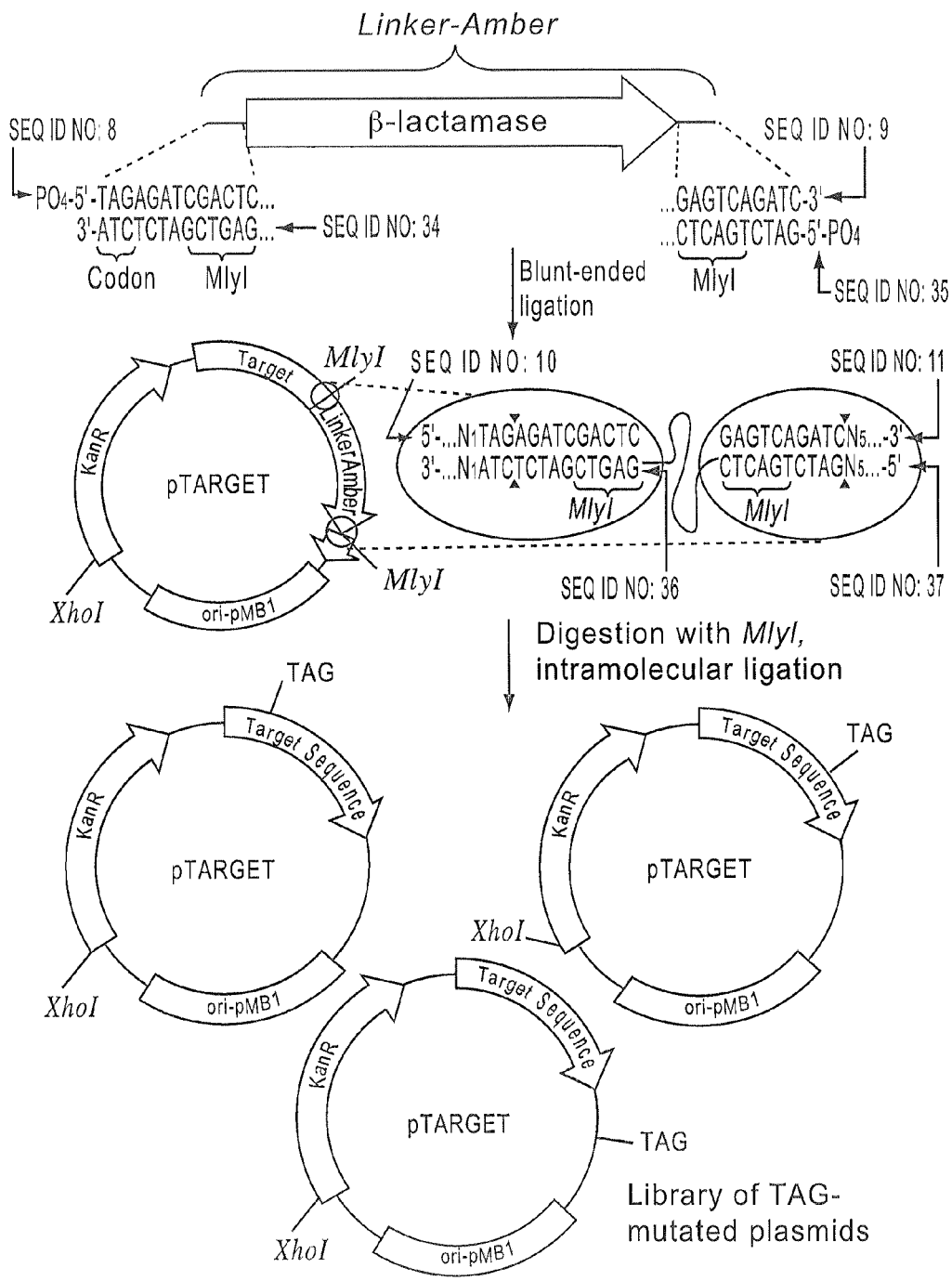

The present invention provides methods and materials for generating codon specific mutations in proteins, wherein the replacement codon is chosen and controlled by the user, although the insertion location can be random. These methods are also referred to as "codon scanning mutagenesis." Because the goal in codon scanning mutagenesis is to probe a protein at multiple codon positions, a plasmid produced in accordance with the invention can be a member of a population of mutant plasmids.

A method of codon specific mutagenesis is provided according to one aspect of the invention. The method comprises the following steps: A plasmid is provided comprising a target open reading frame, a selectable marker, and an origin of replication. A linear transposon fragment is provided comprising a double stranded nucleic acid with first and second ends, a second selectable marker, and two restriction sites, unique to the original plasmid, and located less than 10 base pairs from the 5' and 3' ends of the transposon fragment. Examples of suitable transposon and fragments thereof include the Mu, Tn5, Tn9, and other transposons. The transposon fragment and the first plasmid are reacted in the presence of the cognate transposase enzyme to cause integration of the transposon into the plasmid at random insertion sites, and duplication of N nucleotides, depending on the transposase used. The second plasmid is digested with the restriction enzyme corresponding to the unique site. A collection of randomly linearized plasmids is generated. This collection of plasmids is ligated with a linear double-stranded nucleic acid comprising a second selectable marker capable of selecting correct in-frame ligation events, and additional unique TypeII S restriction sites positioned such that digestions removes N+3 nucleotides the mixture of plasmids, and leaves three new nucleotides in their place to yield a plasmid that encodes a mutant polypeptide.

A method of codon specific mutagenesis is provided in accordance with an aspect of the invention. The method comprises the following steps: A plasmid is provided that comprises a target open reading frame, a selectable marker capable of selecting correct in-frame ligation events, and an origin of replication. A linear transposon fragment is provided comprising a double stranded nucleic acid with first and second ends, a second selectable marker and two unique primer binding sites that differ by greater than 5 degree Tm. Examples of suitable transposon and fragments thereof include the Mu, Tn5, Tn9, and other transposons. The transposon and the first plasmid are reacted in the presence of the cognate transposase enzyme to cause integration of the transposon into the plasmid at random insertion sites, and duplication of N nucleotides, depending on the transposase used. The two primer binding sites are used for inverse PCR with two oligonucleotides that incorporate unique TypeII S restriction sites positioned such that digestions removes N+3 nucleotides the mixture of plasmids, and leaves three new nucleotides in their place.

A method of codon specific mutagenesis is provided in accordance with an aspect of the invention. The method comprises the following steps: A first plasmid is provided comprising a target open reading frame, a first selectable marker, and an origin of replication, wherein the first plasmid does not contain a MlyI restriction site. A linear Mu transposon is provided comprising a double stranded nucleic acid with first and second ends, a second selectable marker, a first MlyI restriction site proximal the first end and a second MlyI restriction site proximal the second end, wherein the first and second ends comprise overhanging DNA sequence (sticky ends). The Mu transposon and the first plasmid are reacted in the presence of MuA transposase to cause integration of the Mu transposon into the plasmid at an insertion site with accompanying removal of the sticky ends and duplication of a five base pair sequence of the first plasmid at the insertion site to form a second plasmid. The second plasmid is digested with MlyI restriction enzyme to form a first linear blunt-ended double-stranded nucleic acid, wherein the nucleic acid comprises the first selectable marker. A codon scar linker comprising a second linear blunt-ended double-stranded nucleic acid with first and second ends, a first MlyI restriction site proximal the first end and a second MlyI restriction site proximal the second end, wherein the first or second end comprises a mutant replacement codon, and wherein the codon scar linker comprises a third selectable marker. The first linear blunt-ended double-stranded nucleic acid is ligated with the codon scar linker to form a third plasmid. The third plasmid with MlyI restriction enzyme to form a third linear blunt-ended double-stranded nucleic acid comprising the mutant replacement codon and first and second ends. The first and second ends of the third linear blunt-ended double-stranded nucleic acid comprising the mutant replacement codon are intramolecularly ligated to form a fourth plasmid, wherein the fourth plasmid encodes a mutant polypeptide.

A method of codon specific mutagenesis is provided in accordance with an aspect of the invention. A first plasmid is provided comprising a target open reading frame, a first selectable marker, and an origin of replication, wherein the first plasmid does not contain a BsgI restriction site. A linear Mu transposon is provided comprising a double stranded nucleic acid with first and second ends, second and third selectable markers, a mutant codon proximal the first end, wherein the first and second ends comprise overhanging DNA sequence, and wherein at least the second selectable marker is in the same translational reading frame as the mutant codon. The Mu transposon and first plasmid are reacted in the presence of Mu transposase to cause integration of the Mu transposon into the plasmid at an insertion site with accompanying removal of the sticky ends and duplication of a five base pair sequence of first plasmid at the insertion site to form a second plasmid. An inverse-polymerase chain reaction (inverse-PCR) is performed employing the second plasmid as a template and first and second oligonucleotide primers, wherein each primer comprises an overhanging nucleic acid sequence and a template binding sequence, wherein the overhanging nucleic acid sequence comprises a BsgI restriction site, wherein the inverse PCR produces a second linear double-stranded nucleic acid. The second linear double-stranded nucleic acid is digested with BsgI restriction enzyme to form a third linear double-stranded nucleic acid, wherein the third double-stranded nucleic acid comprises the mutant replacement codon, the first selectable marker, and first and second ends with overhanging nucleic acid sequence. The third double-stranded nucleic acid is repaired with PHUSION™ polymerase or other suitable proofreading polymerase to form a fourth double-stranded nucleic acid with blunt ends. The fourth double-stranded nucleic acid sequence is intramolecularly ligated to form a third plasmid, wherein the third plasmid encodes a mutant polypeptide.

A method of codon specific mutagenesis is provided in accordance with an aspect of the invention. The method comprises the following steps: A first plasmid is provided comprising a target open reading frame, a first selectable marker, and an origin of replication, wherein the first plasmid does not contain a NotI restriction site. A linear Mu transposon is provided comprising a first double-stranded nucleic acid with first and second ends, a second selectable marker, a first NotI restriction site proximal the first end and a second NotI restriction site proximal the second end, wherein the first and second ends comprise overhanging (sticky-ended) DNA sequence. The Mu transposon and first plasmid are reacted in the presence of MuA transposase to cause integration of the Mu transposon into the plasmid at an insertion site with accompanying removal of the sticky ends and duplication of a five base pair sequence of the first plasmid at the insertion site to form a second plasmid. The second plasmid is digested with NotI restriction enzyme to form a second linear sticky-ended double-stranded nucleic acid, wherein the nucleic acid comprises the first selectable marker. A codon scar linker is provided comprising a third linear double-stranded nucleic acid with first and second ends, a first NotI restriction site proximal the first end, a second NotI restriction site proximal the second end, a mutant replacement codon between the first and second NotI restriction sites, a single BsgI restriction site located adjacent to the first NotI restriction site and between the first NotI restriction site and the mutant replacement codon, a single MlyI restriction site located between the BsgI and the mutant replacement codon, and a single BsaXI restriction site located adjacent to the second NotI site and between the mutant replacement codon and the second NotI restriction site and wherein the codon scar linker comprises a third selectable marker, and wherein the codon scar linker has been digested with NotI restriction enzyme to provide sticky ends. The second linear sticky-ended double-stranded nucleic acid is ligated with the codon scar linker to form a third plasmid. The third plasmid is digested with BsgI and MlyI restriction enzymes to form a fourth linear sticky-ended double-stranded nucleic acid comprising the mutant replacement codon. The sticky ends of the second linearized sticky-ended double-stranded nucleic acid are blunted to form a first linear blunt-ended double-stranded nucleic acid. The first and second ends of the first linear blunt-ended double-stranded nucleic acid comprising the mutant replacement codon and first and second ends are ligated intramolecularly to form a fourth plasmid. The fourth plasmid is digested with BsaXI restriction enzyme to form a fifth linear sticky-ended double-stranded nucleic acid comprising the mutant replacement codon. The sticky ends of the fifth linear sticky-ended double-stranded nucleic acid are blunted to form a second linearized blunt-ended double-stranded nucleic acid with first and second ends. The first and second ends of the second linear blunt-ended double-stranded nucleic acid comprising the mutant replacement codon are ligated intramolecularly to form a fifth plasmid, wherein the fifth plasmid encodes a mutant polypeptide.

The replacement codon used can be any codon encoding any amino acid, naturally or non-naturally occurring. In some embodiments, the amino acid is one of the twenty standard amino acids. The replacement codon can be selected from the group consisting of a codon encoding a standard amino acid and the amber stop codon (TAG). In some embodiments, the replacement codon encodes alanine. In some embodiments, the replacement codon encodes the amber stop codon (TAG). An amber stop codon can be used to incorporate modified, non-standard and non-naturally occurring amino acids. Examples of such amino acids include fluorescent, photoreactive, pegylated, and glycosylated amino acids, as well as those displaying unnatural functional groups such as azides, ketones, and alkynes. The introduction of unnatural functional groups such as aryl-ketones allow one to site-specifically label proteins with hydrazide or aminoxy-bearing fluorescent dyes which are extremely useful in protein diagnostics or biophysical studies. Likewise, site-specific attachment of polyethylene glycol to therapeutic proteins such as interferon or erythropoietin can improve pharmacokinetic properties. One particularly useful non-natural amino acid is para-benzoylphenylalanine (pBpa), which allows probing of protein structure and interaction through its photoaffinity label.

The method of the invention can be used to insert one or more mutations into a protein or other polypeptide. In some embodiments, the ratio of transposon to first plasmid yields about one transposon insertion per first plasmid. The method can be repeated with the product of the first round of mutagenesis to yield at least a second replacement codon insertion. In some embodiments, the first and second replacement codons are identical to each other. In some embodiments, the first and second replacement codons are not identical but encode the same amino acid. When codons encode the same amino acid, they can encode any amino acid. In some embodiments, the encoded amino acids are alanine or cysteine.

The first and second replacement codons can be different from each other. The first and second replacement codons can encode different amino acids. In some embodiments, the first and second amino acids differ from each other in the charge of their end or side group. For example, the amino acids can be selected from the group consisting of aspartic acid, glutamic acid, lysine, and arginine. A salt bridge can be introduced using such mutations.

Insertion of one or more mutant codons that results in a change in a change of amino acid residue in a polypeptide sequence allows for the creation of intra and intermolecular protein linkages such as disulfide bonds and salt bridges. For example, introduction of one or more cysteine residue through a mutant codon(s) can create a disulfide bond where one did not exist before. Insertion of one or more mutant codons encoding for positively and/or negatively charged amino acid residues can create salt bridge(s) where one did not exist before. Hydrophobic and non-charged interactions can also be introduced and/or probed, for example, through mutant scanning with tryptophan or phenylalanine. Proline-scanning mutagenesis can be used for alpha-helix disruption. Enzymatic function can be studied with the codon specific mutagenesis techniques of the invention as can drug receptor interactions.

The selectable markers, including sequence encoding the same, used in the nucleic acid constructs of the invention can differ from one another. Examples of selectable markers compatible with the methods of the invention include an antibiotic resistance protein or auxotrophy protein. In some embodiments, at least one of the selectable markers comprises a promoter and a start codon (ATG).

The methods of the invention can further comprise growing an organism transformed with a plasmid on a selectable medium corresponding to one or more of the selectable markers of the plasmid. The mutant polypeptide encoded by an open reading frame containing at lease one mutant replacement codon can be expressed by the organism.

Where degeneracy in the genetic code occurs, a codon providing the desired efficiency of expression in the organism used can be employed. The target open reading frame for mutation can be comprised by a gene, a fragment thereof, or any other nucleic acid sequence. A mutant polypeptide comprising a mutant replacement codon, wherein the mutant replacement codon is an amber stop codon (TAG) can be expressed employing an artificial tRNA system or other suitable means for coding a non-natural amino acid at the amber stop codon. Any non-naturally occurring amino acid can be employed. In some embodiments, the non-natural amino acid is para-benzoylphenylalanine (pBpa). In some embodiments, a naturally occurring amino acid is employed that has been modified in a non-naturally occurring manner. For example, an amino acid can have a functional group that allows for subsequent peglyation.

Kits including one or more material of the invention are provided that can be used to carry out the methods of the invention in whole or part.

A nucleic acid or nucleotide sequence thereof includes one or more nucleotides. Exemplary nucleic acids include RNA, DNA, any combination thereof. Nucleic acids can include both naturally occurring as well non-naturally occurring nucleotides, and encompass ribonucleic acid nucleotides, as well as deoxyribonucleic acid nucleotides. When a nucleic acid is recited it refers generically to DNA and RNA unless the recitation explicitly states that the nucleic acid is a specific one, e.g., DNA or RNA. If a nucleic acid refers to a sequence that contains thymine (t), that does not necessarily indicate that the nucleic acid is DNA; in some embodiments the nucleic acid is RNA and/or DNA. Similarly, if a nucleic acid refers to a sequence that contains uracil (u) that does not necessarily indicate that the nucleic acid is RNA; in some embodiments the nucleic acid is DNA and/or RNA.

The nucleic acid molecules relevant to the invention can readily be obtained in a variety of ways, including, without limitation, chemical synthesis, cDNA or genomic library screening, expression library screening, and/or PCR amplification of cDNA. These methods and others useful for isolating such DNA are set forth, for example, by Sambrook et al., "Molecular Cloning: A Laboratory Manual," Cold Spring Harbor Laboratory Press, Cold Spring Harbor, N.Y. (1989), by Ausubel, et al., eds., "Current Protocols In Molecular Biology," Current Protocols Press (1994), and by Berger and Kimmel, "Methods In Enzymology: Guide To Molecular Cloning Techniques," vol. 152, Academic Press, Inc., San Diego, Calif. (1987).

Chemical synthesis of a nucleic acid molecule can be accomplished using methods well known in the art, such as those set forth by Engels et al., Angew. Chem. Intl. Ed., 28:716-734 (1989). These methods include, inter alia, the phosphotriester, phosphoramidite and H-phosphonate methods of nucleic acid synthesis. According to one embodiment, nucleic acids larger than about 100 nucleotides in length can be synthesized as several fragments, each fragment being up to about 100 nucleotides in length. The fragments can then be ligated together to form a full length nucleic acid encoding the polypeptide. One method is polymer-supported synthesis using standard phosphoramidite chemistry.

Alternatively, the nucleic acid can be obtained by screening an appropriate cDNA library prepared from one or more tissue source(s) that express the polypeptide, or a genomic library from any subspecies. The source of the genomic library may be any tissue or tissues from a mammalian or other species believed to harbor a gene encoding a protein relevant to the invention. The library can be screened for the presence of a cDNA/gene using one or more nucleic acid probes (oligonucleotides, cDNA or genomic DNA fragments that possess an acceptable level of homology to the gene or gene homologue cDNA or gene to be cloned) that will hybridize selectively with the gene or gene homologue cDNA(s) or gene(s) that is (are) present in the library. The probes preferably are complementary to or encode a small region of the DNA sequence from the same or a similar species as the species from which the library was prepared. Alternatively, the probes can be degenerate. After hybridization, the blot containing the library is washed at a suitable stringency, depending on several factors such as probe size, expected homology of probe to clone, type of library being screened, number of clones being screened, and the like. Stringent washing solutions can be low in ionic strength and are used at relatively high temperatures, although any suitable washing solution can be used in accordance with the methods of the invention.

Another suitable method for obtaining a nucleic acid in accordance with the invention is the polymerase chain reaction (PCR). In this method, poly(A)+RNA or total RNA is extracted from a tissue that expresses the gene product. cDNA is then prepared from the RNA using the enzyme reverse transcriptase. Two primers typically complementary to two separate regions of the cDNA (oligonucleotides) are then added to the cDNA along with a polymerase such as Taq polymerase, and the polymerase amplifies the cDNA region between the two primers.

The invention provides for the use of isolated, purified or enriched nucleic acid sequences of any length, In some embodiments, the nucleic acid is from 15 to 500 nucleotides in length, 15 to 100 nucleotides in length, 15 to 50 nucleotides in length, 15 to 30 nucleotides in length, 30 to 300 nucleotides in length, or 45 to 200 nucleotides in length, or 45 to 100 nucleotides in length, which have sequence that corresponds to a portion of one of the nucleic acids or nucleotide sequences described herein. The nucleic acid can be at least 5, 6, 7, 8, 9, 10, 12, 15, 17, 20, 22, 25, 30, 35, 40, 50, 100, 150, 200, 250, 300, 350, 400, 450, 500, 1000, 10,000, 50,000, 100,000 or more nucleotides in length, or 100,000, 75,000, 50,000, 10,000, 5,000, 1000, 750, 500, 250, 200, 100, 50, 40, 30, 25, 22, 20, 17, 15, 12, 10, 9, 8, 7, 6, 5, or fewer nucleotides in length. The nucleic acid can have a length in a range from any one of the above lengths to any other of the above lengths including endpoints.

A nucleic acid in accordance with the invention can be 25%, 30%, 35%, 40%, 45%, 50%, 55%, 60%, 65%, 70%, 75%, 80%, 82%, 84%, 86%, 88%, 90%, 91%, 92%, 93%, 94%, 95%, 96%, 97%, 98%, 99%, or 100% identical to any reference sequences provided herein. A nucleotide that hybridizes under stringent conditions to a nucleotide described herein can be employed. Unless otherwise specified, percent identities for nucleic acids and amino acid sequences are determined as follows: Percent identity of two nucleic acid sequences or two amino acid sequences is determined using the algorithm of Karlin and Altschul (Proc. Natl. Acad. Sci. USA, 87:2264-2268 (2002), modified as in Karlin and Altschul et al., Proc. Nat. Acad. Sci. USA, 90:5873-5877 (1993). Such an algorithm is incorporated into the NBLAST and XBLAST programs of Altschul et al., J. Mol. Biol. 215: 403-410 (1990). BLAST nucleotide searches are performed with the NBLAST program, score=100, wordlength=1, to obtain nucleotide sequences with a percent identity to a nucleic acid employed in the invention. BLAST protein searches are performed with the XBLAST program, score=50, wordlength=3, to obtain amino acid sequences with a percent identity to a reference polypeptide. To obtain gapped alignments for comparison purposes, Gapped BLAST is utilized as described in Altschul et al., Nucleic Acids Res., 25:3389-3402 (1997). When utilizing BLAST and Gapped BLAST programs, the default parameters of the respective programs (e.g., XBLAST and NBLAST) are used. See <www.ncbi.nih.gov>.

Unless otherwise specified, a nucleic acid and nucleic acid probe can include one or more nucleotide analogs, labels or other substituents or moieties so long as the base-pairing function is retained. The nucleic acid probe can comprise a detectable label, such as a radioactive or fluorescent label. A variety of other detectable labels are known to those skilled in the art. Unless otherwise specified, where the sequence for a given strand is provided, the invention also includes its complement in addition or in the alternative.

In connection with nucleic acid hybridization, the term "specifically hybridizes" indicates that the probe hybridizes to a sufficiently greater degree to the target sequence than to a non-target sequence, e.g., at a level which allows ready identification of probe/target sequence hybridization under selective hybridization conditions. "Selective hybridization conditions" refer to conditions that allow such differential binding. Similarly, the terms "specifically binds" and "selective binding conditions" refer to such differential binding of any type of probe, and to the conditions that allow such differential binding.

Variables can be adjusted to optimize the specificity of a nucleic acid probe, including changes in salt concentration, temperature, pH and addition of various compounds that affect the differential affinity of GC vs. AT base pairs, such as tetramethyl ammonium chloride. [See Current Protocols in Molecular Biology, Ausubel et al. (Editors), John Wiley & Sons.] Hybridization conditions should be sufficiently stringent such that there is a significant difference in hybridization intensity between alleles, and preferably an essentially binary response, whereby a probe hybridizes to only one of the alleles. Hybridizations can be performed under stringent conditions that allow for specific binding between an oligonucleotide and a target nucleic acid. Stringent conditions are defined as any suitable buffer concentrations and temperatures that allow specific hybridization of the oligonucleotide and any washing conditions that remove non-specific binding of the oligonucleotide. For example, conditions of 5×SSPE (750 mM NaCl, 50 mM Na Phosphate, 5 mM EDTA, pH 7.4) and a temperature of 25-30° C. are suitable for allele-specific probe hybridizations. The washing conditions can range from room temperature to 60° C.

Polypeptides or fragments thereof can be expressed in an expression vector in which a gene or coding segment thereof or related construct thereof is operably linked to a native or other promoter. The promoter can be a eukaryotic promoter for expression in a mammalian cell. The transcription regulation sequences typically include a heterologous promoter and optionally an enhancer that is recognized by the host. The selection of an appropriate promoter, for example trp, lac, phage promoters, glycolytic enzyme promoters and tRNA promoters, depends on the host selected. Commercially available expression vectors can be used. Vectors can include host-recognized replication systems, amplifiable genes, selectable markers, host sequences useful for insertion into the host genome, and the like.

The expression construct can be introduced into a host cell in a number of ways depending upon the particular construction and the target host, for example, fusion, conjugation, transfection, transduction, electroporation, or injection, as described in Sambrook, supra. A wide variety of host cells can be employed for expression of the gene or coding segment thereof or related construct thereof including both prokaryotic and eukaryotic. Suitable host cells include bacteria such as E. coli, yeast, filamentous fungi, insect cells, mammalian cells, typically immortalized, e.g., mouse, CHO, human and monkey cell lines and derivatives thereof. Host cells can be selected to process the translated product to produce an appropriate mature polypeptide. Processing includes glycosylation, ubiquitination, disulfide bond formation, and general post-translational modification.

The protein can be isolated by conventional means of protein biochemistry and purification to obtain a substantially pure product, i.e., 80, 95 or 99% free of cell component contaminants, as described in Jacoby, Methods in Enzymology Volume 104, Academic Press, New York (1984); Scopes, Protein Purification, Principles and Practice, 2nd Edition, Springer-Verlag, New York (1987); and Deutscher (ed), Guide to Protein Purification, Methods in Enzymology, Vol. 182 (1990). If the protein is secreted, it can be isolated from the supernatant in which the host cell is grown. If not secreted, the protein can be isolated from a lysate of the host cells.

In addition to substantially full-length polypeptides expressed by genes or coding segments thereof, the invention includes use of biologically active fragments of the polypeptides, or analogs thereof, including organic molecules that simulate the interactions of the peptides. Biologically active fragments include any portion of the full-length polypeptide that confers a biological function on the expressed product, including ligand binding and antibody binding. Ligand binding includes binding by nucleic acids, proteins or polypeptides, small biologically active molecules or large cellular structures. In some embodiments, the polypeptide is at least 5, 6, 7, 8, 9, 10, 12, 15, 17, 20, 22, 25, 30, 35, 40, 50, 100, 150, 200, 250, 300, 350, 400, 450, 500, 1000, 10,000, 50,000, 100,000 or more amino acids in length, or 100,000, 75,000, 50,000, 10,000, 5,000, 1000, 750, 500, 250, 200, 100, 50, 40, 30, 25, 22, 20, 17, 15, 12, 10, 9, 8, 7, 6, 5, or fewer amino acids in length. A polypeptide can have a length in a range from any one of the above lengths to any other of the above lengths including endpoints. A polypeptide in accordance with the invention can be 25%, 30%, 35%, 40%, 45%, 50%, 55%, 60%, 65%, 70%, 75%, 80%, 82%, 84%, 86%, 88%, 90%, 91%, 92%, 93%, 94%, 95%, 96%, 97%, 98%, 99%, and 100% identical to reference sequence provided herein.

The following examples further illustrate the invention but, of course, should not be construed as in any way limiting its scope.

EXAMPLE 1

This example demonstrates creation of a simple and general method for codon scanning mutagenesis.

To make way for the library construction process and to simplify the digestion and transposition steps, a targeting plasmid that is high copy number, small in size, and has convenient cloning sites for the ligation of open reading frames that are to be scanned is created. In preparation for an alanine scanning experiment, the gene encoding E. coli uracil phosphoribosyl-transferase (UPRT) is inserted into the plasmid (pTARGET), which is derived from the popular cloning vector pKQ and is very small. Of the total 2888 base pairs (bp) that constitutes that plasmid backbone, the kanamycin resistance marker and promoter is 1020 bp, the origin of replication is 845 bp, leaving approximately 400 bp of sequence outside of the target gene that is not essential for plasmid maintenance. Such a small target plasmid is beneficial in the transposition reaction because it will direct most of the transposon insertions to the target DNA sequence as opposed to non-functional sequence. Any plasmids containing insertions in the origin of replication or kanamycin resistance marker will therefore not survive growth on kanamycin agar. If one considers the non-functional DNA and the size of the UPRT gene, there are approximately 1000 different places in which to break (and mutate) the plasmid.

All cloning procedures are performed according to standard methods (Sambrook, J. et al., (1989) Molecular Cloning, a Laboratory Manual. (Cold Spring Harbor Laboratory Press, Cold Spring Harbor, N.Y.). For routine cloning and library construction GENEHOGS® (Invitrogen) are used, which is a high efficiency, phage resistant derivative of DH10B E. coli. Oligonucleotides can be obtained from Integrated DNA Technologies. Restriction enzymes can be obtained from New England Biolabs and MBI Fermentas. PCR reactions are carried out using PHUSION™ high-fidelity DNA polymerase (New England Biolabs) in a MJ Research DNA engine thermocycler. Site-directed mutagenesis is conducted using the Quickchange method (Papworth, et al., (1996) Stratagies 9, 3-4.) or enzymatic-inverse PCR (Stemmer, W. P. et al., (1992) Biotechniques 13, 214-20). DNA sequence data are obtained using ABI Model 3730 sequencers. DNA and protein sequence information are analyzed by the DNAStar suite of sequence analysis programs, and by the use of Web based programs NCBI-BLAST (Altschul, et al., (1990) J Mol Biol 215, 403-10.) and Clustal W. Transposition reactions are performed using 100 ng of modified transposon DNA sequence and 200 ng of targeting plasmid according to the recommended protocol for the Hyper MuA transposase system (Epicentre Biotechnologies). After heat inactivation, the library is electroporated into GENEHOGS® and selected on chloramphenicol plates with dilutions indicating the library size.

Protein expression is also done in GENEHOGS® fermented in LB broth. Vectors pTrcHisA and pBAD can be used for expression, which do not require a chromosomal copy of T7 RNA polymerase. His-tagged proteins are purified on PROBOND™ resin (Invitrogen) or His grab HISGRAB™ plates (Pierce) according to the manufactures protocols. Western blots are performed by wet transfer to nitrocellulose membranes and probed with monoclonal mouse primary antibodies (Novagen) and secondary antibodies conjugated to alkaline phosphatase (Santa Cruz Biotech). Blots are developed with ECF (GE Healthcare) and imaged on a Storm Imager using the blue laser. The subsequent ligation after linker removal is straightforward as the reaction is intramolecular and CaO be done in dilute solution in order to prevent concatamers from forming.

The targeting plasmids are modified using traditional Quikchange mutagenesis to sequentially remove all MlyI recognition sites in the plasmid backbone. The MlyI site in the origin of replication is first removed by a single base nucleotide mutation (in an attempt to not disrupt the origin of replication). This mutated plasmid is then used as a template to remove the second MlyI site in the kanR gene. This process results in a silent mutation and does not disrupt the protein amino acid sequence of the resistance protein. Absence of these sites allows for the ligation assembly that will insert the codon "scars" as MlyI is designed to be unique to the entire plasmid. The target DNA sequence is flanked by unique BamHI, EcoRI, and SalI sites that allow direct subcloning of inserts (and libraries) into the convenient expression vectors pBADmycHisA and pTrcHisA (Invitrogen) vector, among many others. High level protein expression can then follow the library construction process. A process as described in Chin, J. W., et al. (2003) Science 301, 964-7 can be employed.

As an alternative to other approaches (Qian, Z. et al., (2005) J Am Chem Soc 127, 13466-7; Zhao et al., (1997) Nucleic Acids Res 25, 1307-8.), random double-stranded breaks are created in the target gene using a transposable element flanked by a Type II restriction cleavage site that "cuts outside" leaving blunt ends. The Mu transposon/transposase system has a very limited target DNA sequence specificity and can carry virtually any selectable marker located between the transposase recognition sites (R1 and R2). Furthermore when the transposition reaction is conducted in vitro, insertion occurs only once, with each plasmid molecule ultimately carrying one selectable marker gene in a random position. In the MuA system, the flanking sequence outside of the transposase recognition sequence is permissive to mutation and can be modified to contain paired MlyI sites (a type II restriction enzyme that cuts five by downstream of the sequence 5'-GAGTC-3'). The transposition process also creates a five by duplication in the target gene. Upon digestion with MlyI, which is oriented to "reach outside," into this target DNA sequence duplication, the entire selectable marker is removed resulting in a clean, blunt-ended excision of three by (N2, N3, and N4) from the original target sequence. When this removal occurs in the correct frame, a single amino acid codon will be removed and at the same time, leave DNA ends open to ligation of any new sequence. An example of codon scanning mutagenesis is shown in FIGS. 1A-1B.

Using the commercially available HYPERMU™ <CHL-1> transposon (Epicentre Biotechnologies) as a template, two new MlyI restriction sites are introduced at the appropriate flanking locations by PCR. These mutations are just outside of the transposase recognition site, and do not interfere with the mobility of the transposon. This new transposon, called MlyI-transposon, is cloned into a plasmid to provide a renewable source upon removal with BgIII digestion and gel purification. This produces a DNA fragment that has the appropriate "sticky" ends for recognition and processing by the MuA transposase. The integrity of the MIyI-transposon can be verified by full-length sequencing.

The activity of the MlyI-transposon for random insertion into a target gene is tested. 100 ng of prepared transposon DNA is combined with 200 ng of pTARGET and incubated with one unit of HYPERMU™ MuA Transposase (Epicentre Biotechnologies) for three hours, after which the reactions are inactivated, electroporated into GENEHOGS® E. coli cells (Invitrogen), and plated on LB agar plates containing 50 .mu.g/mL kanamycin (to select for the plasmid) and 35 .mu.g/mL chloramphenicol (to select for the transposon). Using this amount of DNA and under these conditions, about 20,000 colony forming units are obtained, each representing a unique transposition event. In order to verify that the MlyI-transposon can be excised as planned, and that it did indeed insert at random positions, seven individual colonies are miniprepped, along with a the starting plasmid control, and digested them with XhoI-MlyI. These plasmids represent the intermediates depicted in FIG. 1A. The transposon fragment (about 1200 bp) is excised from the transformants. A gel showing that the remaining fragments of the digest are of random size, indicates that the position of insertion is random. DNA sequencing of these plasmids reveal that all insertion points are random and located in the target gene. However, only two of the seven are inserted in the appropriate reading frame. Finally, the remaining colonies from two of the library plates (about 6000 colonies) are swept into LB liquid media containing kanamycin and chloramphenicol, and grown overnight to amplify. This pooled library is digested with MlyI alone, and as expected produced only two fragments: the transposon fragment and vector DNA (minus one codon). The vector DNA band in this gel actually represents a complex mixture of the original pTARGET/UPRT with a perfect, single double-strand break in a random position. The ends of these linearized plasmids contain 5'-phosphates and can be ligated to the codon scar linkers.

Once a clean, randomly placed, double stranded break has been created in the coding sequence (along with concomitant removal of three bp), the next step is to ligate in a new codon sequence. A new selectable marker in used in place of what had been used. This selectable marker can also carry MlyI restriction sites but oriented such that upon removal, they actually leave three bp rather than remove them. In essence, this is the reverse of the first process—removal of this segment of DNA will leave a "scar" on the DNA that represents the new replacement codon. This selectable marker is different from the CAT gene found on the transposon to help prevent cross-contamination in these two library construction steps. Clones displaying the new resistance phenotype should carry the desired linker and should generate the appropriate scar. Using pUC19 as a template, the β-lactamase (bla) gene is PCR-amplified along with its promoter and terminator. In addition, the PCR primers generate ends that have the appropriately positioned MlyI sites. Initially created are two linkers; one that leaves an alanine coding "GCG" scar (Linker-Ala), and one that leaves a universal unnatural amber stop codon "TAG" scar (Linker-Amber). These linkers carry 5'-phosphophates and are ready for blunt-ended ligation (FIG. 1C). Creation of a full set of 21 linkers for the full genetic code (plus one unnatural) can be accomplished using a different set of reverse oligos.

The Linker-Ala DNA fragment is ligated into the randomly broken DNA from the above transposition (that is derived from a combined 3000 independent colonies). Many different ligation conditions can be employed such as adjustment of vector and insert ratios, addition of polyethylene glycol (PEG) and lower ATP concentrations, to increase ligation efficiency. Satisfactory results can be obtained from ligations containing 5% PEG 4000 using linker fragments generated from PCR reactions containing PHUSION™ DNA polymerase (New England Biolabs). In addition, pretreatment of the target DNA with Shrimp Alkaline Phosphatase (MBI-Fermentas) is a precaution for background reduction. After overnight ligation, this DNA is electroplated into GENE-HOGS®, and the transformants are plated on LB agar containing 50 µg/mL kanamycin (to select for the plasmid) and 100 µg/mL ampicillin (to select for the linker). These conditions can provide 2200 independent clones from 100 ng of vector (pTARGET) DNA. In one embodiment, eighteen of these independent transformants are chosen and grown in selective liquid culture, mini-prepped the plasmid DNA, and analyzed for the insertion of the Linker-Ala fragment by restriction digest. Digestion with XhoI-MlyI excises the linker from all clones and produces two other random-sized fragments. This demonstrates that the linker positioning is indeed random, and that it can be selectively removed. Furthermore, 100% of the colonies contain the linker due to the fact that the transformants are selected with ampicillin. This second round of selection is critical on what would be a low-probability ligation event (blunt intermolecular). These intermediate plasmids represent those depicted in FIG. 1C, the penultimate stage in the library construction process. The remaining colonies are swept into LB broth, amplified, the DNA extracted. The last step in the codon scanning process is the removal of the linker DNA fragment with MlyI digestion and relegation of the plasmid backbone. The difference with the first digestion is that in the step, the removal actually leaves a new codon (in this case for alanine). This MlyI digest can be performed on the pooled library plasmids to give the mature library, which can be verified by DNA sequencing.

A method to pre-select or "purify" the gene libraries containing mutations in the correct frame can be employed. Strategies for reading frame selection can include consist of creating a gene fusion to a selectable marker such as green-fluorescent protein, chloramphenicol acetyl transferase (CAT) or β lactamase (bla). (Lutz, S. et al., (2002) Protein Eng 15, 1025-30.) In these systems, any introduced frame-shift in the open reading frames will eliminate fusion protein production and the selectable phenotype, thus allowing easy enrichment of the in-frame members. According to codon scanning mutagenesis, there is no net addition or subtraction of nucleotides to the coding sequence (three nucleotides are removed and replaced with three new ones). However, this process can occur out of frame. If a new codon (for example TAG) replaces three nucleotides that are out of frame, it will result in a mutation, just not the desired one. Because the actual frame of the gene is always maintained in the libraries, the conventional reading frame selections described by others would not work. Selection can be employed to insure that only desired mutations are obtained.

Figure 2:
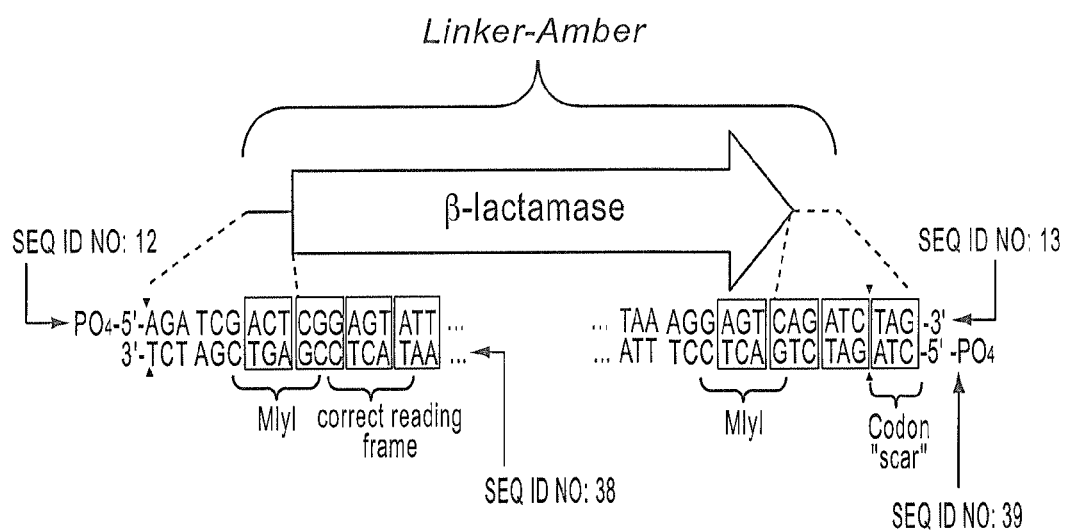
FIG. 2 shows a codon scar linker in accordance with the invention.

One example of a reading frame selection is to modify the codon scar linker such that the resistance marker does not carry its own promoter and start codon, and instead would require that it be expressed as an in-frame, C-terminal fusion protein to the target protein. Thus, correct blunt-ended ligation to the target sequence would render cells resistant to ampicillin. If this ligation occurred out of frame, or in the wrong orientation, there would be no reporter protein expressed, and these undesirables could be removed by ampicillin selection. The codon scar is placed at the 3'-end of this linker (after the resistance marker), so as not to interfere with selection, and the intervening sequence adjusted such that by definition if the linker ligates in the correct frame, the codon scar is subsequently be placed in the correct frame. A second generation linker can be created by PCR amplification of the bla gene (minus a start codon and promoter) to produce a new linker Linker-Amber-RFS (FIG. 2). A single PCR reaction using phosphorylated oligonucleotides to generate a fragment ready for ligation can be employed. The resulting clones are selected by plating separately on LB/Kan plates and LB/Kan+Amp plates. Comparison of the colony forming units on these two conditions should give a rough approximation of the effectiveness of the selection. In an embodiment, there are 1/16th as many colonies on the dual selection plates (because only one out of six ligated into the correct reading frame). Sample colonies surviving the dual antibiotics are then sequenced to observe if the frame selection did indeed work.

Mutant libraries do not need to be large. Normally random or saturation mutagenesis of proteins demands complexities that exceed the transformation efficiency of E. coli (~$10^9$ colony forming units/µg of DNA). Because the method according to the invention produces "clean" libraries, with no redundancy, far fewer independent clones are needed to insure full coverage of the theoretical diversity. For example, a codon scanning experiment can be performed on an extremely large protein of 5000 amino acids in length. In fact, very few proteins are this size, but for the sake of argument, imagine such a scanning experiment on an open reading frame of 15,000 bp (5000 codons). There are 15,000 different positions for a transposon to insert in such a gene, and a transposon can insert in two different orientations (forward and reverse with respect to the ORF), giving a total theoretical diversity of 30,000. Even such a large protein one would only involve about 276,000 independent clones to obtain library coverage with a confidence level of 99.99% in a Poisson sampling (Ladner, R. C. (1996) in Phage Display of Peptides and Proteins (Academic Press, San Diego), pp. 151-194). Such a library size represents only a ten-fold increase from the initial test-run of 20,000 colonies using 200 ng of DNA. This number is easily obtainable by standard E. coli transformation. Of this library, only one sixth would be true mutants in the correct frame of the protein and codon insertion in the other five frames would result in unpredictable mutation depending on the sequence surrounding the insertion site. With the implication of a reading frame selection, the naïve libraries can be "pre-purified" of all codon mutations (⅚th of the original library) that occurred in the incorrect frame. These libraries are quite small and manageable in comparison to those created using other methods. Thus they can be applied to screens rather than selections.

Beta-lactamase and the tetracycline efflux pump TetA(B) are two example of proteins that can be scanned using codon scanning mutagenesis. Vector libraries generated can be used to accept a series of residue specific linkers. For example, a TetA(B)/tryptophan library, and separately a TetA(B)/glycine library, etc., for a total of 40 different libraries can be constructed. This represents a sequence diversity of approximately 40,000 individual defined mutants which is outside of the capability of site-directed mutagenesis. Once these are constructed, they are plated separately on LB agar containing 20 or 200 µg/mL ampicillin or tetracycline. Controls that use non-selective plates can also be performed. A comparison of the number of colony forming units on the selective versus the nonselective plates for each amino acid gives a percentage of detrimental mutants. These results can then be used to rank the amino acids in the genetic code for propensity to inactivate these two proteins. Such information is a useful, fundamental constant of protein structure and function, and can be used in designing future libraries.

Codon scanning mutagenesis can make use of proteins that have selectable (ampicillin or tetracycline resistance) or counterselectable (5-FU sensitivity) activity. Such use is not a requirement but rather allows rapid assessment of protein function and calculate the fraction of inactive or active variants by comparing colony forming units in selective versus non selective environments.

EXAMPLE 2

Figure 3:
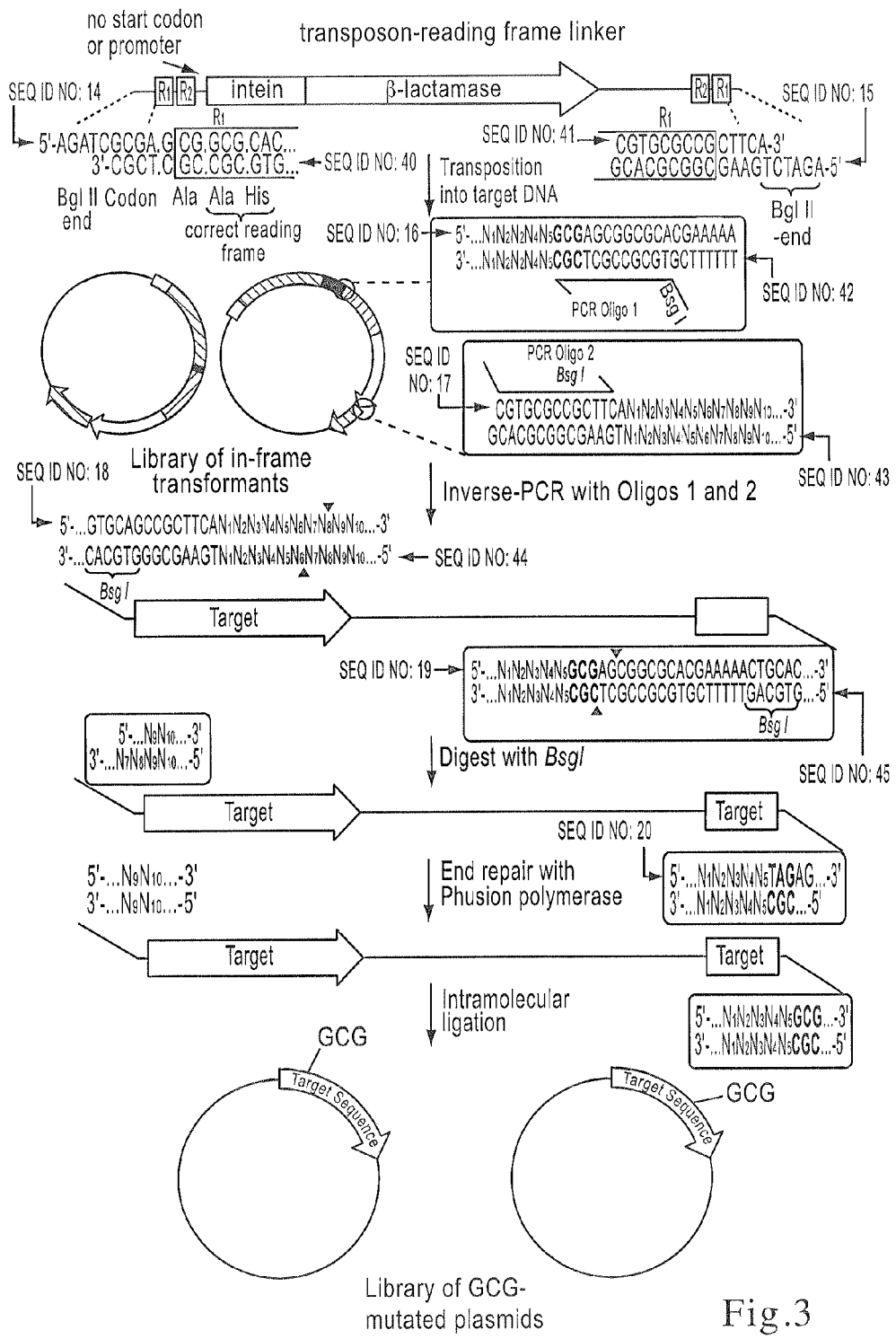
FIG. 3 shows stages of codon specific mutagenesis in accordance another embodiment of the invention.

This example demonstrates a variation on the codon scanning mutagenesis technique described in Example 1. The three steps of codon removal, scar replacement, and frame selection are combined in the first transposition step. Another modified transposon is constructed by PCR such that it contains the TAG codon sequence at the outside edge. The opposing end of the transposon is a slightly different sequence on the outside base (FIG. 3). After transposition, the resulting colonies are combined and the pooled DNA containing new sequence are used as a primer binding site for inverse-PCR amplification of the entire plasmid backbone, and in the process, insertion of two new appropriately positioned BsgI sites. Despite the fact that the primers are very similar, this PCR reaction will not fire unless primed with two different oligonucleotides as the bases at the 3'-end are different. The use of BsgI is employed to provide more "reach" into the flanking target DNA in order to remove sequence on one side. BsgI cuts 16 bp downstream of its recognition site, and there are no sites present in the targeting plasmid. BsgI digestion of the resulting PCR fragment generates ends with 3' overhangs. Removal of these overhangs to generate blunt ends can be accomplished using a polymerase with 3'→5' exonuclease activity (this can all be done in the PCR reaction). These blunt ends can be ligated (in dilute solution) to directly create the codon replacement.

Frame selection can also be incorporated into the transposition step by removing the promoter and start codon from the selection marker in the transposon. In such a system, the marker is expressed as a C-terminal fusion protein to the gene of interest, which should only occur where the transposon inserts in the correct frame. Read-through of the R1 and R2 recognition sites should not be a problem as these do not contain stop codons. For purposes of frame selection, Beta-lactamase is used because the transposon can carry any interior sequence. Other suitable selectable markers could be used. Two selection markers can be used; one that can be used for frame selection and another as a simple insertional selection. The efficiency of the frame selection can be ascertained by comparing colony forming units on LB chloramphenicol plates and ampicillin+chloramphenicol plates. There should be approximately six times as many colonies on the plates lacking ampicillin selection.

EXAMPLE 3

This example demonstrates another variation of the technique of Example 1 as an example of the codon scanning mutagenesis technique in accordance with the invention. The gene encoding *E. coli* uracil phosphoribosyl-transferase (UPRT) is inserted into the plasmid (pTARGET/UPRT), which is derived from the popular cloning vector pKQ and is very small. Such a small target plasmid helps direct the majority of the transposon insertions to the target DNA sequence as opposed to non-functional sequence. Plasmids containing insertions in the origin of replication or kanamycin resistance maker should not survive growth on kanamycin agar. If one considers the non-functional DNA and the size of the UPRT gene, there are approximately 1000 different places in which to break (and mutate) the plasmid. These targeting plasmids are further modified using a series of traditional site-directed mutagenesis reactions to sequentially remove all BsgI, MlyI, BsaXI, and NotI recognition sites in the plasmid backbone. Absence of these sites allows for the subcloning processing of the libraries. The target DNA sequence is flanked by unique BamHI, SalI, and EcoRI sites that allow direct subcloning of inserts (and libraries) into the convenient expression vectors pBADmycHisA and pTrcHisA (Invitrogen) vector, among many others. High level protein expression can then follow the library construction process.

Cloning procedures are performed according to standard methods. For cloning and library construction, GENE-HOGS® *E. coli* cells (Invitrogen) are used, which is a high efficiency, phage resistant derivative of DH10B *E. coli*. Oligonucleotides can be obtained from Integrated DNA Technologies. Restriction enzymes can be obtained from New England Biolabs and MBI Fermentas. PCR reactions are carried out using PHUSION™ high-fidelity DNA polymerase (New England Biolabs) in a MJ Research DNA engine thermocycler. Site-directed mutagenesis are conducted using the Quickchange method 7 or enzymatic-inverse PCR9. DNA and protein sequence information will be analyzed by the DNAStar suite of sequence analysis programs, and by the use of Web based programs NCBI-BLAST (Altschul, S. F., Gish, W., Miller, W., Myers, E. W. & Lipman, D. J. Basic local alignment search tool. J Mol Biol 215, 403-410 (1990)) and Clustal W. Transposition reactions are performed using 100 ng of modified transposon DNA sequence and 200 ng of targeting plasmid according to the recommended protocol for the Hyper MuA transposase system (Epicentre Biotechnologies). After heat inactivation, the library is electroporated into Genehogs® *E. coli* and selected on chloramphenicol plates with dilutions indicating the library size.

Protein expression is also done in GENEHOGS® *E. Coli* fermented in LB broth. The vectors pTrcHisA and pBAD can be employed for expression, which do not require a chromosomal copy of T7 RNA polymerase. His-tagged proteins are purified on PROBOND™ resin (Invitrogen) or HISGRAB™ plates (Pierce) according to the manufactures protocols. Western blots are performed by wet transfer to nitrocellulose membranes and probed with monoclonal mouse primary antibodies (Novagen) and secondary antibodies conjugated to alkaline phosphatase (Santa Cruz Biotech). Blots are developed with ECF reagent (GE Healthcare) and imaged on a Storm Imager using the blue laser.

After subjecting the libraries to a one of the frame selections (described above), the library can be confirmed by sequencing about 100 colonies of each finished library to help insure that there are only single codon replacements, and that there are no other mutations. Based on the size of the target gene (UPRT), 918 independent clones can be used to scan this gene with a 99% confidence level. This number of clones should be maintained throughout all cloning and subcloning steps in the process. A Mu transposon/transposase system as described in Example 1 can be employed with following modifications. Using the commercially available HYPERMU™ <CHL-1> transposon (Epicentre Biotechnologies) as a template, two NotI restriction sites are introduced at the appropriate flanking locations by PCR. These mutations are just outside of the transposase recognition site, and do not interfere with the mobility of the transposon. This transposon, called NotI-transposon, is cloned into a plasmid to provide a renewable source upon removal with BglII digestion and gel purification. This produces a DNA fragment that has the appropriate "sticky" ends for recognition and processing by the MuA transposase. The integrity of the NotI-transposon has been verified by full-length DNA sequencing.

Figure 4:
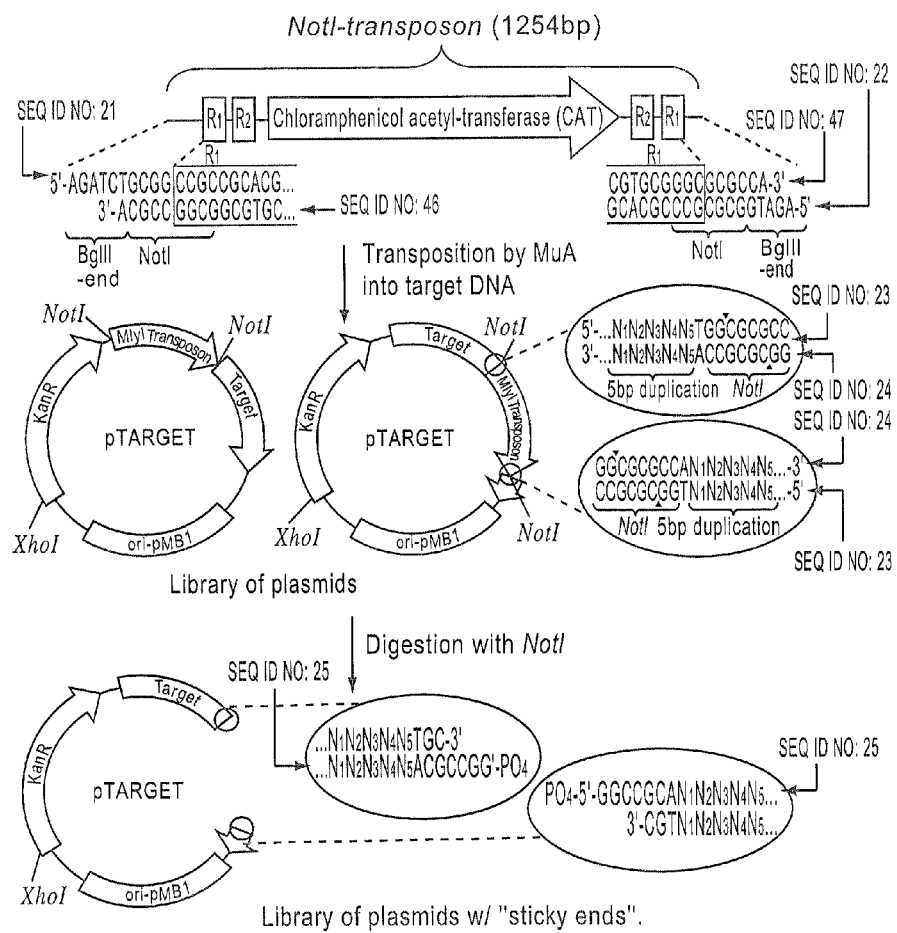
FIGS. 4 and 5 show stages of codon specific mutagenesis in accordance with yet another embodiment of the invention.

100 ng of the prepared transposon DNA are combined with 200 ng of pTARGET and incubated with one unit of HYPERMU™ MuA Transposase (Epicentre Biotechnologies) for three hours, after which the reactions are inactivated, electroporated into GENEHOGS® E. Coli cells (Invitrogen), and are plated on LB agar plates containing 50 µg/mL kanamycin (to select for the plasmid) and 35 µg/mL chloramphenicol (to select for the transposon). Using this amount of DNA and under these conditions, about 20,000 colony forming units can be obtained, each representing a unique transposition event. Increasing the size of this process should easily yield about $10^5$ transformants. In order to verify that the NotI-transposon can be excised as planned, and that it did indeed insert at random positions, ten individual colonies are mini-prepped from the library and are digested with XhoI-MlyI. The transposon fragment (about 1200 bp) is excised from every transformant. The remaining fragments of the digest are of random size (because the location of the XhoI site is fixed), indicating that the position of transposon insertion is random. DNA sequencing of these plasmids can be employed to verify the results. The remaining colonies from two of the library plates (about 6000 colonies) are swept into LB liquid media containing kanamycin and chloramphenicol, and grown overnight to amplify plasmid DNA. This pooled library is digested with NotI alone and produces only two fragments: the transposon fragment and the vector DNA. The vector DNA band in this gel actually represents a complex mixture of the original pTARGET/UPRT with a perfect, single double-strand break in a random position. While they are all the same size, they are actually different fragments. The ends of these linearized plasmids contain 5'-phosphates and can be ligated with DNA segments containing compatible NotI sticky ends. This is the next step in the library construction process (FIG. 4).

Once a clean, randomly placed, double stranded break has been created in the coding sequence, a new fragment can be ligated in place. However, there is a small amount of "scrap DNA" left from the transposon insertion. One approach is to ligate a new selectable marker in place of the transposon that was removed. This secondary antibiotic selection helps guarantee that all clones will contain the desired mutation. This selectable marker is designed to also contain asymmetric type IIS restriction endonuclease sites oriented such that the linker can be removed along with this "scrap DNA". In addition to removing this transposon DNA, the restriction process removes three base pairs from the parent sequence and leaves a three base pair "scar", or codon, behind. This selectable marker different from the chloramphenicol marker found on the transposon to help prevent cross-contamination in these two library construction steps. Clones displaying the new resistance phenotype carry the desired linker and can indeed generate the appropriate scar. Clones surviving this second selection step should contain the new mutant codon. This is true for multiple rounds of scanning.

Figure 5:
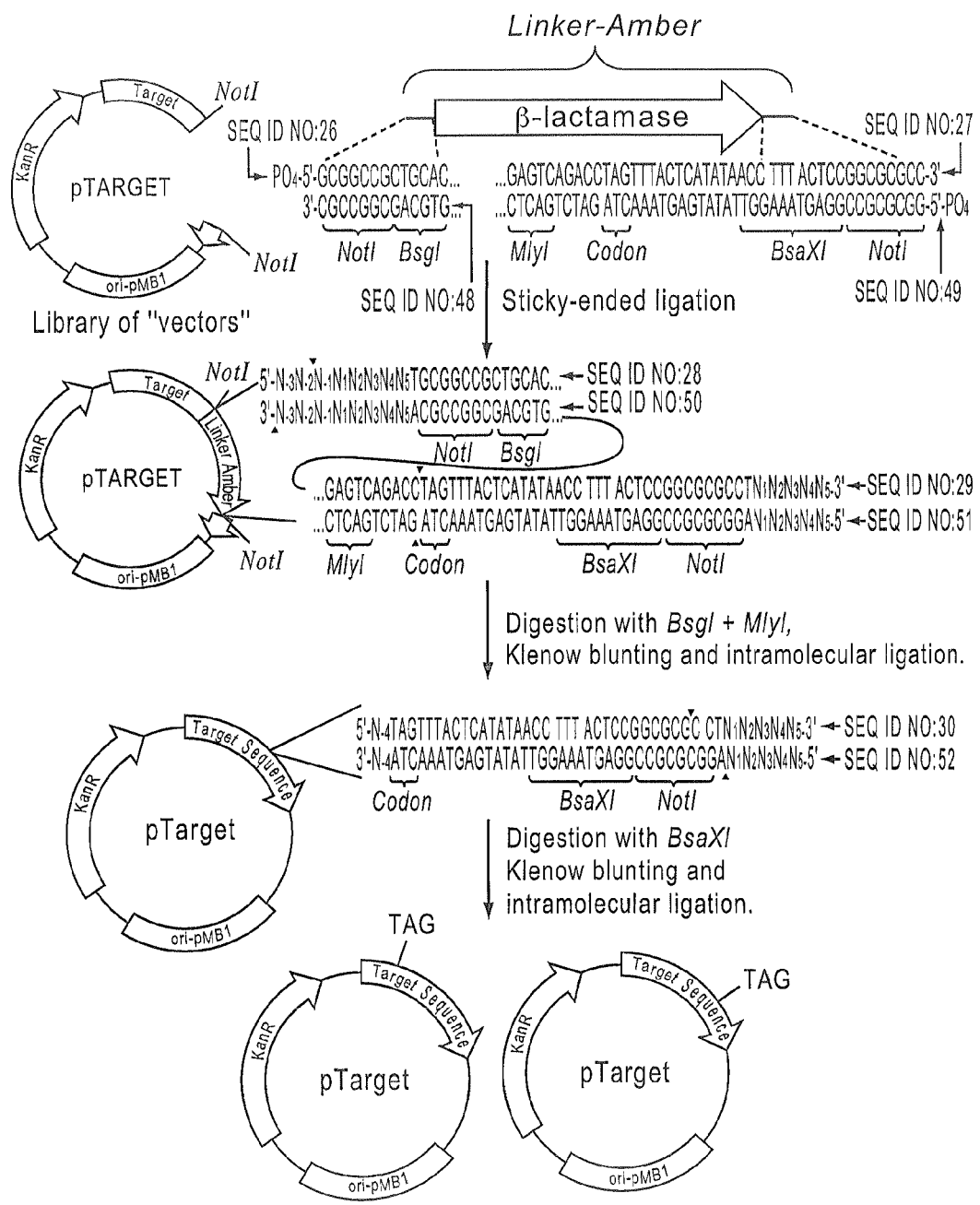

To create a codon scar linker, the Beta-lactamase gene (bla) is PCR amplified with overhanging oligos to introduce the restriction sites shown in FIG. 5. In one embodiments, twenty-one of these linkers, all of which are identical except for the codon scar. The codons are chosen based upon the preferred codon preference in E. coli, and correspond to one of the twenty genetically encoded amino acids or an amber stop codon, TAG. The Linker-Amber DNA fragment (which leaves a TAG scar) is ligated into the randomly broken DNA from the above transposition (that is derived from a combined 6000 independent colonies). After overnight ligation, this DNA is electroplated into E. coli, and plated the transformants of LB agar containing 50 µg/mL kanamycin (to select for the plasmid) and 100 µg/mL ampicillin (to select for the linker). These conditions provide about 6000 independent clones from 100 ng of vector (PTARGET) DNA. 10 of these independent transformants are picked and grown in selective liquid culture, isolated plasmid DNA, and analyzed for the insertion of the fragment by restriction digest. XhoI-NotI excises the linker from all clones and produces two other random-sized fragments (due to the fixed position of the XhoI site). This demonstrates that the linker positioning is random and that it can be selectively removed. Furthermore, 100% of the colonies contain the linker (and mutation), due to the fact that the transformants are selected with ampicillin. The remaining colonies are swept into LB broth, amplified, and the DNA extracted.

The pooled plasmid library containing the Linker-Amber segment is then processed by two rounds of restriction digestion, end polishing, and blunt ended ligation. As depicted in FIG. 5, the plasmids containing the Linker-Amber are first digested with BsgI and MlyI and blunted the ends using Klenow polymerase. This DNA is then re-ligated (blunt, intramolecular) to remove the bulk of the linker while replacing three bp of the target sequence with a new TAG codon. This process is quantitative as it is intramolecular and can routinely produce about $10^5$ transformants.

Figure 6:
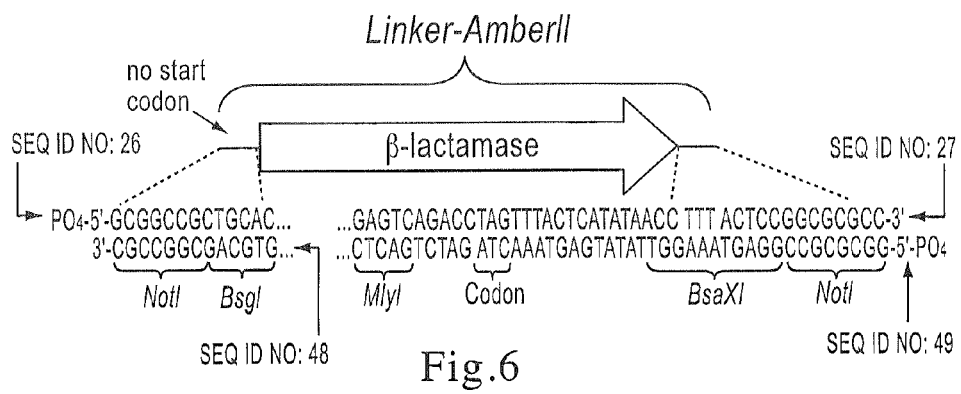
FIGS. 6 and 7 show codon scar linkers in accordance with the invention.

One example of a reading frame selection is to modify the codon scar linker such that the resistance marker does not carry its own promoter and start codon, and instead would require that it be expressed as an in-frame, C-terminal fusion protein to the target protein. Thus, correct ligation to the target sequence would render cells resistant to ampicillin. If this ligation occurred out of frame, or in the wrong orientation, there would be no reporter protein expressed. This linker is created by PCR amplification of the Beta-lactamase gene (minus a start codon and promoter) to produce the linker Linker-Amber II (FIG. 6).

As a test, this linker segment is ligated into a series of test plasmids to determine if this approach was valid for the library construction. This linker sequence is positioned in four different orientations with respect to the target gene (in-frame forward, out of frame forward, in-frame reverse, out of frame reverse). These represent the four possibilities that can occur upon ligation into a library of vectors. When plated on plates containing ampicillin, only the clone containing the in-frame ligation grows. When used in a library construction protocol, there are one sixth as many colonies on the dual selection plates (because only one out of six ligated into the correct reading frame). If this is not the case, the amount of ampicillin included in the media can be titrated to an amount where it is removing ⅚th of the clones.

An alternative reading frame selection system (pPPV) from Professors Michael Hecht and David Wood at Princeton University can be employed. The pPPV system is based upon the combined action of a fast cleaving intein and the selectable auxotrophic marker, thymidylate synthase, thyA, which rescues thymine auxotropy. (Bradley, L. H., et al., Protein Eng Des Sel 18, 201-207 (2005).) With this system, the library is removed from the selectable marker quickly after it is synthesized. Provided that this intein-thyA fusion is originally placed in frame with a ribosome binding site and start codon, functional thymidylate synthase is expressed and renders cells able to grow in the absence of thymine. This method is independent of the structural state of the fusion protein as it is self-cleaved before the protein can aggregate.

Figure 7:
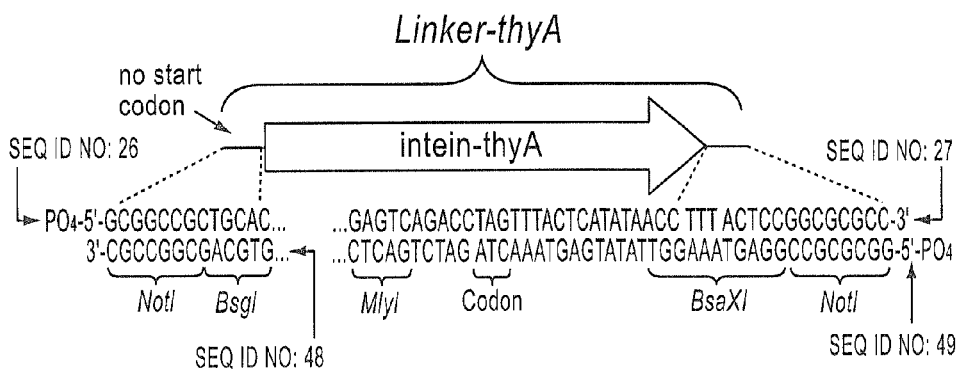

BsgI, MlyI, and BsaXI sites are first removed from the intein-thyA sequence. The intein-thyA fragment is then PCR amplified to incorporate the appropriately positioned TAG codon scar and restriction sites, including flanking NotI sites for ligation into the vector library. This linker (FIG. 7) is ligated into a target vector in four different frames as indicated above. These clones are then plated on M9 agar+kanamycin with or without supplemental thymine (50 μg/mL). As this is an auxotrophy based selection, the selection pressure can be adjusted by incubation time and temperature.

Figure 8:
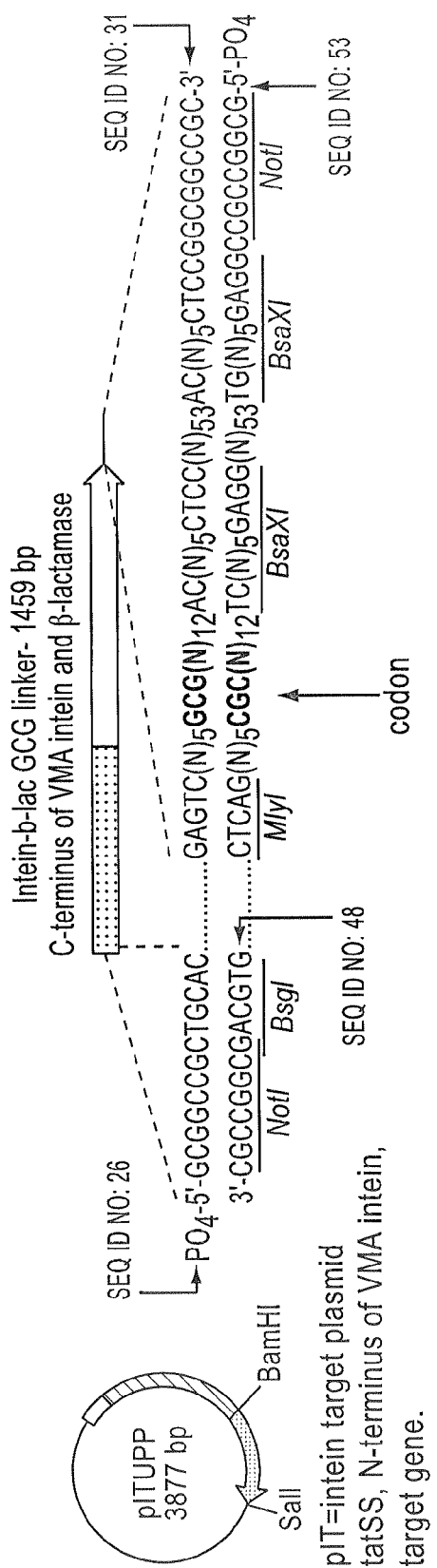
FIG. 8 shows a codon scar linker in accordance with the invention.
Figure 9:
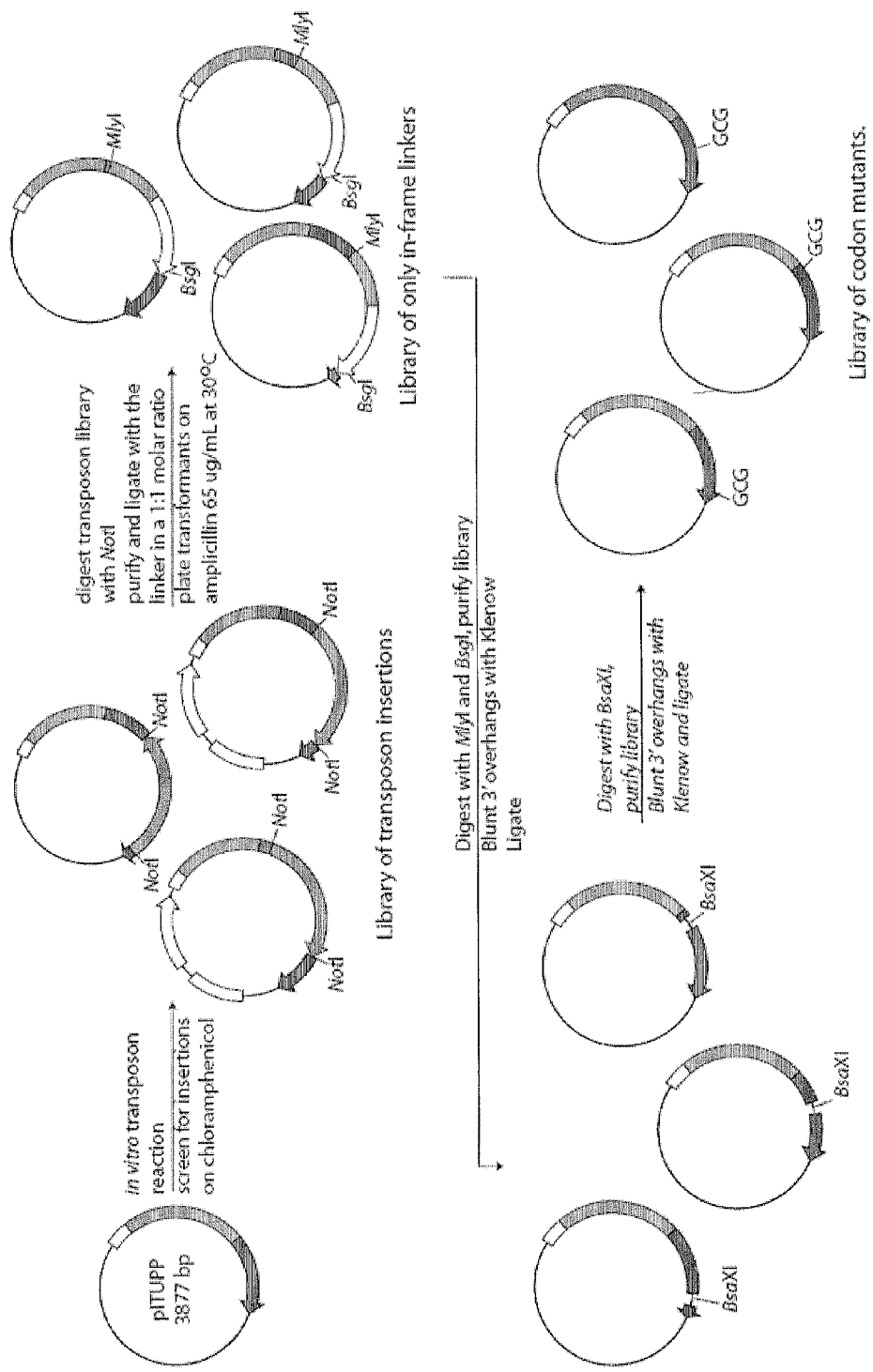
FIG. 9 shows stages of codon specific mutagenesis in accordance with still another embodiment of the invention.

A variation of the codon scanning mutagenesis described in Example 3 can be performed using the 3877 bp plasmid pITUPP and the 1459 bp Intein b-lac-GCG linker (FIG. 8). An overview of the technique is shown in FIG. 9. The sequence for the pITUPP plasmid is provided in the sequence listing (SEQ ID NO: 1). Examples of DNA Sequences of the VMA-intein-Blac TAG (Amber) codon scar linker (SEQ ID NO: 2; DNA Sequence of VMA-intein-Blac NNN codon scar linker, wherein NNN is any three nucleotides or otherwise defined in the specification) and of intein-ThyA-GCG (alanine) Linker (SEQ ID NO: 3; DNA Sequence of intein-ThyA-NNN codon scar linker: wherein NNN is any three nucleotides or otherwise defined in the specification) are also provided in the sequence listing. Examples of amino acid translations of the linkers are further provided. Examples of preferred codons for growth in *E. coli* include GCG (alanine), TTT (phenylalanine), TTA (leucine), ATT (isoleucine), GTG (Valine), AGC (Serine), CCG (Praline), ACC (Threonine), TAT (Tyrosine), CAT (Histidine), CAG (Glutamine), AAA (Lysine), GAT (Aspartic Acid), GAA (Glutamic Acid), TGC (Cysteine), TGG (Tryptophan), CGT (Arginine), GGC (Glycine) codon scar linker, ATG (Methionine) codon scar linker, AAC (Asparagine) codon scar linker, and TAG (Amber) codon scar linker.

EXAMPLE 4

This example demonstrates that the codon scanning mutageneis techniques of the present invention can be used for high-throughput alanine scanning to probe enzymatic function. A functional test of full-gene alanine scanning mutagenesis using the *E. coli* uracil-phosphoribosyltransferase gene (UPRT) is performed. This gene can be used as a counterselectable marker as expression is quite toxic in the presence of 5-fluourouracii (5-FU). A genetic selection for this enzyme is created based on a knockout strain of *E. coli*, GH:AUPRT (kindly provided by Prof. Jason Chin of the MRC-LMB/Cambridge). When transformed with an empty kanamycin resistant plasmid, this strain shows a clear phenotype of robust growth on agar containing up to 10 μg/mL 5-FU. When transformed with pTARGET/UPRT and grown on kanamycin (to force maintenance of the plasmid), however, cells are sensitive on as little as 2 μg/mL 5-FU, due to the presence of the constitutive UPRT activity. This counterselection provides a test for scanning the entire UPRT gene with alanine codons to determine critical residues for enzyme function. Any alanine mutation in a critical residue should result in a selectable phenotype.

Using the developed counter-selection, alanine scanning mutagenesis is performed on the UPRT gene to look for loss-of-function mutants. Libraries are generated in normal GENEHOGS®. After subjecting the libraries to a frame selection (see Example 1), the library is verified by sequencing about 20 colonies of the finished library to insure that there are single GCG codon replacements, and that there are no other mutations. Twenty clones give some indication of the quality. Based on the size of the UPRT gene, at least 918 independent clones may be needed to scan this gene with a 99% confidence level. This number of clones should be maintained throughout all cloning and subcloning steps in the process. After creation of the alanine scanned pTARGET/UPRT, the plasmid library is transformed into GH:AUPRT cells, and the cells are plated on LB kanamycin+5 μg/mL 5FU. Any colonies capable of growth should harbor copies of the UPRT gene that are inactive, presumably from mutation of a critical residue to alanine. This alanine scanning experiment represents a very simple test of Codon Scanning Mutagenesis, and should pave the way to many other interesting projects. Other protein targets such as GFP or β-lactamase can be subjected to similar treatment and serve as additional proof-of-principle experiments.

EXAMPLE 5

This example demonstrates that the codon scanning mutageneis techniques of the present invention can be used for high-throughput cysteine, arginine, or other amino acid scanning to probe enzymatic function. The Beta-lactamase reporter protein which can be functionally selected in vivo (using resistance to ampicillin) and very accurately assayed in vitro (using nitrocefin) is used. It can serve as a rapid route to results that provide information not known about structure and function. Whole gene cysteine scanning: foot-printing applied to trans-membrane proteins and protein folding. A library of proteins containing single cysteine mutations such that they can be mapped for accessibility using thiol protection assays can be constructed. This approach will quickly generate structural information of protein-protein and protein-ligand interaction epitopes and membrane protein domains.

Another UPRT library can be constructed in which cysteine scanning instead of alanine scanning as described in Example 4 is performed using a cysteine linker (e.g., codon is TGC). With the library constructed and verified functional, thiols can be mapped as has been described by Silverman, J. A. et al., J Biol Chem 277, 30968-30975 (2002). *E. coli* cells are grown expressing the mutant genes in LB media, the cells are harveted, and resuspend in 50 mM sodium bicine buffer, pH 8.6. Aliquots of these cells are then be reacted with 10 mM iodoacetamide at room temperature and stopped with excess Beta-mercaptoethanol at 2, 10, and 20 minutes. A negative control containing no iodoacetamide can also be included. These cells are then be lysed and the mutant proteins purified under denaturing conditions using ProBond nickel affinity resin (Invitrogen) according to the manufacturers instructions. The UPRT is appended with a 6-histidine tag (SEQ ID NO: 33). The purified, denatured proteins are then subjected to NTCB cleavage (which specifically cleaves peptides at cysteine residues) as has been described by Jacobson, G. R., et al., J Biol Chem 248, 6583-6591 (1973); Wu, J. et al., Anal Biochem 258, 268-276 (1998); Wu, J., et al., Protein Sci 7, 1017-1028 (1998). The cleaved peptides are then resolved on a 20% tricine SDS-PAGE gel, transferred to a nitrocellulose membrane, and imaged by Western blotting using an anti-His-tag antibody. Alternatively, this collection of peptides can be analyzed by mass spectrometry.

A distribution of peptide fragments corresponding to cleavage at residue positions that are not protected from the reagents can be obtained. Theoretically, a correctly processed negative control library in which none of the cysteines are protected should produce a distribution of every possible truncated peptide. For example, the UPRT protein is 209 amino acids. The library can contain 209 different cysteine mutants which when truncated will give the same number of peptides of increasing size (1aa, 2aa, 3aa, etc). This mixture of peptides can serve as a molecular weight size marker, and the protein that did receive alkylation protection should contain peptides that are absent. Those peptides that are absent will be indicative of a residue in the native protein which is "exposed" by virtue of its alkylation. Comparison of a protein sample that was thiol-protected in the native state to one that was not gives a "protection factor" for each residue, thus giving valuable structural information.

A library of the *E. coli* TetA(B) tetracycline efflux pump which is a commonly used selectable marker in molecular biology and a transmembrane protein is created. The gene encoding the TetA(B) efflux pump is amplified from pACYC184 (New England Biolabs) and added a C-terminal 6× histidine affinity tag (SEQ ID NO: 33). This fragment is digested with BamHI and SalI and ligated into similarly digested pTARGET. *E. coli* transformed with this plasmid, pTARGET/TET, are resistant to tetracycline, indicative of a functional protein. Quikchange mutagenesis can be used to silently remove a MlyI site from the TetA(B) gene in order to be compatible with the Codon Scanning Method. This plasmid can in turn be used for the cysteine scanning experiment described in the Experimental Design.

Survivors of the cysteine and arginine scanned libraries can be employed. These represent functional enzymes that contain a single mutation. These clones are separately pooled and the plasmid DNA extracted. These plasmid pools are then used as the targets for additional rounds of scanning to create mixtures which contain two cysteines or two arginines, respectively. These libraries will then be selected again using two different levels of stringency (20 and 200 µg/mL ampicillin), and the survivors isolated. Depending on the percentage of functional mutants that observed (as judged by comparison to non-selective plates), mutagenesis can be continued to include third, fourth, or fifth rounds of cysteine or arginine mutations.

The functional clones from these rounds of mutagenesis are then be picked into 96 deep-well blocks, grown to saturation, and the cells harvested by centrifugation and lysed. Aliquots of the cell lysate are then heated in PCR thermocycler to high temperature (50°, 60°, 70°, or 80°) for 5 minutes. The lysates are then cooled and assayed for hydrolysis of nitrocefin, a chromogenic substrate for Beta-lactamase. Any clones that display enhanced survival at high temperatures (in comparison to wild-type), can be fully sequenced to determine the positions of the mutations. In addition, these clones can serve as parents for future rounds of scanning in which the number of mutations are pressed to a maximum. Potential contributions by disulfide bonds are assayed using Ellman's reagent as described by Riddles, P. W., et al. Anal Biochem 94, 75-81 (1979).

Mutations can be "tuned" that are delivered to the protein. For example, if the three residues that are most likely to destroy function are determined to be proline, tyrosine, and phenylalanine, a custom mix of linkers can be created that is lean in these three codons. This approach can be used to produce enzymes that display enhanced properties.

Other examples of cysteine-scanning include the study of protein folding pathways, by performing similar experiments at different temperatures or in different concentrations of denaturants like urea. Likewise two proteins could be mixed together or a protein and an antibody, and the "protection factor" used to map binding epitopes. Importantly, because the method of detection used in these studies is either a western blot or mass spectrometry, very little protein sample will be required. Clearly, key to these approaches is the ease with which one can access the original library of single cysteine mutants.

EXAMPLE 6

This example demonstrates mapping protein interaction surfaces using scanning photo crosslinking mutagenesis.

Use of unnatural amino acids allows use of an isotopic labeling approach as the incorporation method is completely orthogonal to all other cellular protein synthesis, except for the target protein gene bearing the amber stop codon. Only one peptide in a crude cell lysate will bear the unnatural amino acid and therefore is easily identifiable by a M and M+11 doublet pattern in the mass spectrum. Both labeled and unlabeled amino acid are site-specifically incorporated into glutathione-S-transferase (GST), which is a native homo-dimeric protein and demonstrates that the isotope labels can be used to identify cross-linked peptide fragments in an otherwise complicated mass spectrum. MALDI-TOF analysis of tryptic-digested GST yields a complex mixture of ion peaks. Insertion of pBpa into the tryptic fragment XELGLEFPNLPYYIDGDVKK (SEQ ID NO: 32) (mass=2461.4) can be demonstrated. The same fragment bearing D[11]-pBpa results in the expected mass increasing 11, and a mixture of labeled and unlabeled amino acids yields "doublets" at the two masses, easily identifying the correct fragment. Intriguingly, when photo-crosslinking is performed on these three protein samples and are re-analyze by MALDI-TOF a new set of doublets is obtained corresponding to the newly cross-linked fragments (mass=3029.6 and 3040.8). These peaks most likely represent specific capture of the peptide fragment MFEDR across the protein-protein interface of dimeric GST. These techniques allow for the use of codon scanning mutagenesis in vivo.

As one example, codon scanning mutagenesis is used to sample β-benzoylphenylalanine (pBpa) at every possible position of the gene encoding glutathione S-transferase (GST) from *Schistosoma* japonica. GST is a homodimeric protein and the molecular structure of this protein is very well characterized with the dimer interface illustrated by a crystal structure. The photoaffinity labeling process allows the mapping of any and all of 240 residues for the ability to photo-crosslink across an interface.

In preparation for scanning GST with the photo-crosslinking amino acids pBpa, a pilot scale expression can be performed to determine the minimum amount of culture volume to produce enough protein to be detectable by Coomassie stain. In some embodiments, the volume of the pBpa amino acid is minimized to 2 mL such that it can be replicated in 96-well blocks for high-throughput analysis, ultimately expressing different mutants in each well. Plasmids, such as pSup/pBpa, that allow dual-plasmid expression of proteins containing unnatural amino acids can be used. (Ryu, et al., (2006) Nat Methods 3, 263-5; Farrell, I. S., et al., (2005) Nat Methods 2, 377-84.) Plasmids capable of inserting pAzPhe are also available (Prof. Peter G. Schultz of The Scripps Research Institute) to co-express both the evolved aminoacyl-tRNA synthetase for pBpa and the cognate tRNA, and are compatible with most high copy number expression plasmids. The restriction sites in pTARGET are compatible such that upon subcloning the gene of interest (in this case GST) into pTrcHisA using BamHI and SalI, the target protein are expressed with a C-terminal 6×-His tag (SEQ ID NO: 33) allowing for easy purification. In some embodiments, only 2 mL of culture is used for mutant protein expression.

Figure 10:
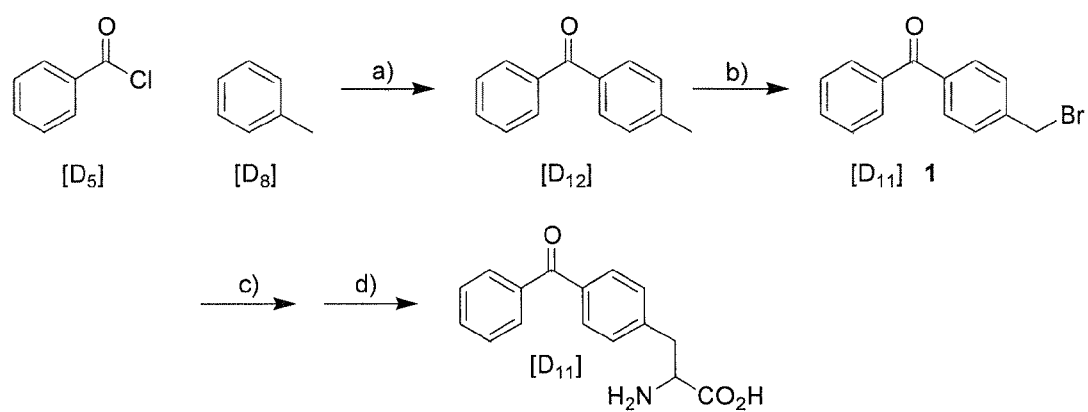
FIG. 10 shows a synthesis of para-benzoylphenylalanine (pBpa) that can be used in accordance with the invention: a) [D8]Toluene, [D5]benzoyl chloride, $AlCl_3$; b) NBS, AIBN, $CCl_4$, reflux overnight; c) Diethylacetamidomalonate NaOEt/EtOH, reflux, 24 h d) 6N HCl reflux, 24 h.

The plasmid, pTARGET/GST is subjected to the library construction protocol (as was described for alanine scanning on UPRT), but rather using the amber codon linker instead to scan TAG codons. The native library is purified by reading frame selection (as described above), and after which, the pooled plasmids will be digested with BamHI and SalI to excise the gene library, ligated into pTrcHisA, and transformed into cells (expression is carried out in GENEHOGS® already harboring the pSUP/pBpa plasmid). Based on the size of the GST gene and a 99% confidence sampling, a diversity of 1010 independent colonies is maintained during the library preparation, including the subcloning steps. After subcloning, individual colonies are picked into 96-well blocks containing 2 mL of LB+100 µg/mL ampicillin+50 µg/mL chloramphenicol. The cultures are grown to saturation and then subcultured with a pin tool to new blocks containing the same media plus 1 mM pBpa (or a 50:50 mixture of labeled/unlabeled pBpa). D[11] p-benzoylphenylalanine (pBpa), a labeled analogue of the photo-crosslinking amino acid (FIG. 10) is synthesized using commercially available labeled starting materials. As the only structural difference is the deuterium substitution, this amino acid can be incorporated site-specifically into proteins using the previously evolved synthetase for pBpa. The cultures are grown at 37° C. to an approximate 00600=0.8 and induced with IPTG to a final concentration of 1 mM, and allowed to grow for 6 hrs. After expression of the mutant libraries, the cells are pelleted in a swinging bucket rotor and prepared for protein purification and assay.

With one mutant, successful crosslinking can be determined by running an SDS-PAGE gel, and new fragments that migrate slower are indicative of a crosslink. In the case of GST which is a 27 kDa protein, successfully crosslinked homodimers show a band at about 54 kDa. The precise location of capture can then be determined by excising the gel band and subjecting it to tryptic digest and MS analysis. High throughput assays can also be employed.

Once the single mutant gene libraries have been expressed in array, they are subjected to MALDITOF analysis. After the cells have been pelleted, they are irradiated at 360 nm (handheld UV is sufficient) for 5 min. The cells are then be lysed by the addition of BugBuster (Novagen), and re-clarified by centrifugation. The mutant 6× His (SEQ ID NO: 33) tagged proteins are purified by high throughput capture on HisGrab Copper coated 96-well plates (Pierce Chemical). Once the crosslinking chemistry of the benzophenone occurs, the protein subunits are covalently and irreversibly trapped with its binding partner, so washing can be done extensively without fear of dissociation. Plates are washed with TBS and 30% ethanol and after washing, proteins are eluted with 200 µl of 0.1% trifluoroacetic acid (TFA) in 50% acetonitrile. This process provides samples in a solution that can be directly spotted onto MALDI plates for analysis. 6 MI of this protein sample (~10 pmol/MI) is mixed with 6 MI of matrix (10 µg/MI, sinapinic acid in 50% acetonitrile:0.05% TFA) in an eppendorf tube and vortexed. From this solution 2 MI is spotted to the MALDI plate yielding approximately 10 pmol of standard protein. The MALDI instrument is set up for high-throughput analysis and can "shoot" approximately 100 samples in 30 min.

Figure 11:
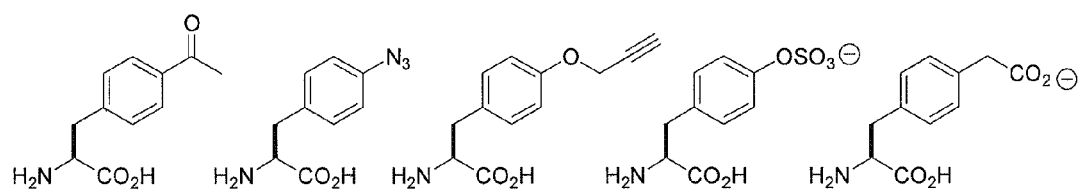
FIG. 11 shows examples of non-naturally occurring amino acids that can be used in accordance with the invention.

In the case of GST, "hits" should include a double in size of the protein (27 kDa to 54 kDa) in the spectrum. A first pass screen such as this is useful for deciphering which of the 1010 mutants contain pBpa mutations in dimer interface positions. After hits have been identified, one can return to the master 96-well blocks to identify the position of the unnatural amino acid by sequencing. These clones can also be subjected to trypsin digestions/MS-MS analysis to determine the actual site of crosslinking and potentially glean structural information of the protein complexes. The negative control for this experiment is wild-type 6×-His (SEQ ID NO: 33) tagged GST (containing no photo-crosslinker). The positive control is the Phe 52, a mutant that can also be used for testing the isotopically encoded pBpa. Examples of other non-naturally occurring amino acids that can be employed are shown in FIG. 11.

An alternate strategy for the detection of crosslinks is to perform an ELISA-type experiment in which there are actually two species of GST in solution; one containing a pBpa mutation and a C-terminal 6×-His tag (SEQ ID NO: 33), for example, and another wild-type sequence fused to an alternative epitope such as a the streptavidin-binding Nano-TAG (55). This mixture can be irradiated and then captured on HisGrab plates just as described above. After crosslinking, the proteins are then be washed and probed with streptavidin-alkaline phosphatase conjugate. The immobilized proteins can be washed with strongly denaturing buffer such as 8M urea which will not affect the binding to the copper coated plates but allow the His-tagged proteins to remain. This process can eliminate interaction between a 6×-His (SEQ ID NO: 33) and Nano-tagged proteins, except for covalently bonded proteins that resulted from a successful crosslink. After washing and probing, the wells are developed by the addition of the substrate p-Nitrophenyl Phosphate (PNPP) and the wells are read in a plate reader at 505 nm. This feature of denaturing the protein complexes allows most of the ELISA signals to be very unambiguous—essentially either signal or no signal—because of the extremely stringent wash conditions. This type of an approach has both advantages and disadvantages over detection by MALDI-TOF. An ELISA experiment has a higher throughput capability, allowing rapid processing of thousands of samples. In addition because it is a covalent interaction, there should be an extremely strong difference between positive and negative readout results. This approach can be the method of choice in situations where the protein binding partners are known, but overall atomic structure is not. Applications of the technique include structural characterizations of multi-protein assemblies such as the proteasome or G-protein signaling networks.

All references, including publications, patent applications, and patents, cited herein are hereby incorporated by reference to the same extent as if each reference were individually and specifically indicated to be incorporated by reference and were set forth in its entirety herein.

The use of the terms "a" and "an" and "the" and similar referents in the context of describing the invention (especially in the context of the following claims) are to be construed to cover both the singular and the plural, unless otherwise indicated herein or clearly contradicted by context. The terms "comprising," "having," "including," and "containing" are to be construed as open-ended terms (i.e., meaning "including, but not limited to,") unless otherwise noted. Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein, is intended merely to better illuminate the invention and does not pose a limitation on the scope of the invention unless otherwise claimed. No language in the specification should be construed as indicating any non-claimed element as essential to the practice of the invention.

Preferred embodiments of this invention are described herein, including the best mode known to the inventors for carrying out the invention. Variations of those preferred embodiments may become apparent to those of ordinary skill in the art upon reading the foregoing description. The inventors expect skilled artisans to employ such variations as appropriate, and the inventors intend for the invention to be practiced otherwise than as specifically described herein.

Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

In the methods and kits of the invention, substitution of restriction enzyme, transposon, and other components can be carried out without departing from the scope of the invention.

What is claimed is:

1. A method of codon-specific mutagenesis, the method comprising:

providing a first plasmid comprising a target open reading frame, a first reading-frame selectable marker, and an origin of replication, wherein the first plasmid does not contain a BsgI restriction site;

providing a linear Mu transposon comprising a double stranded nucleic acid with first and second ends, second and third selectable markers, a mutant codon proximal the first end, wherein the first and second ends comprise overhanging DNA sequence (sticky ends), and wherein at least the second selectable marker is in the same translational reading frame as the mutant codon;

reacting the Mu transposon and first plasmid in the presence of MuA transposase to cause integration of the transposon into the plasmid at an insertion site with accompanying removal of the sticky ends and duplication of a five base pair sequence of first plasmid at the insertion site to form a second plasmid;

performing an inverse-polymerase chain reaction (inverse-PCR) employing the second plasmid as a template and first and second oligonucleotide primers, wherein each primer comprises an overhanging nucleic acid sequence and a template binding sequence, wherein the overhanging nucleic acid sequence comprises a BsgI restriction site, wherein the inverse PCR produces a second linear double-stranded nucleic acid;

digesting the second linear double-stranded nucleic acid with BsgI restriction enzyme to form a third linear double-stranded nucleic acid, wherein the third double-stranded nucleic acid comprises the mutant replacement codon, the first reading-frame selectable marker, and first and second ends with overhanging nucleic acid sequence;

repairing the third double-stranded nucleic acid with a proofreading polymerase to form a fourth double-stranded nucleic acid with blunt ends; and ligating the fourth double-stranded nucleic acid sequence intramolecularly to form a third plasmid, wherein the third plasmid encodes a mutant polypeptide.

2. The method of claim 1, wherein the replacement codon is selected from the group consisting of a codon encoding a standard amino acid and the amber stop codon (TAG).

3. The method of claim 1, wherein the replacement codon encodes alanine.

4. The method of claim 1, wherein the replacement codon encodes the amber stop codon (TAG).

5. The method of claim 1, wherein the ratio of transposon to first plasmid yields about one transposon insertion per first plasmid.

6. The method of claim 1, wherein the method is repeated to yield at least a second replacement codon insertion.

7. The method of claim 6, wherein the first and second replacement codons are identical.

8. The method of claim 6, wherein the first and second replacement codons encode the same amino acid.

9. The method of claim 8, wherein the amino acids alanine or cysteine.

10. The method of claim 6, wherein the first and second replacement codons are different.

11. The method of claim 6, wherein the first and second replacement codons encode different amino acids.

12. The method of claim 11, wherein the first and second amino acids differ in the charge of their end group.

13. The method of claim 12, wherein the amino are selected from the group consisting of aspartic acid, glutamic acid, lysine, and arginine.

14. The method of claim 1, wherein a gene comprises the target open reading frame.

15. The method of claim 1, wherein the first, second, and third selectable markers differ from one another.

16. The method of claim 1, wherein the first, second, and third selectable markers each encode an antibiotic resistance protein or auxotrophy protein.

17. The method of claim 1, wherein at least one of the selectable markers comprises a promoter and a start codon.

18. The method of claim 1, further comprising growing an organism transformed with a plasmid of claim 1 on a selectable medium corresponding to one or more of the selectable markers of the plasmid.

19. The method of claim 1, further comprising expressing the mutant polypeptide encoded by an open reading frame containing at least one mutant replacement codon of the third plasmid of claim 1.

20. The method of claim 19, wherein the expressing comprises expressing a mutant polypeptide comprising a mutant replacement codon, wherein the mutant replacement codon is an amber stop codon (TAG), and wherein the expressing comprises an artificial tRNA system for coding a non-natural amino acid at the amber stop codon.

21. The method of claim 20, wherein the non-natural amino acid is para-benzoylphenylalanine (pBpa).

22. The method of claim 1, wherein the replacement codon is the amber stop codon (TAG) encoding non-natural or non-standard amino acids selected from the group consisting of fluorescent, photoreactive, pegylated, and glycosylated amino acids and amino acids modified with a functional group.

23. The method of claim 22, wherein the functional group is selected from the group consisting of azides, ketones, and alkynes.

* * * * *

SEQUENCE LISTING

```
<160> NUMBER OF SEQ ID NOS: 53

<210> SEQ ID NO 1
<211> LENGTH: 3877
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 1
aagcttttgc cattctcacc ggattcagtc gtcactcatg gtgatttctc acttgataac      60 cttattttg acgagggaa attaataggt tgtattgatg ttggacgagt aggaatcgca       120
gaccgatacc aggatcttgc catcctatgg aactgcctcg gtgagttttc tccttcatta     180
cagaaacggc tttttcaaaa atatggtatt gataatcctg atatgaataa attgcagttt     240
catttgatgc tcgatgagtt tttctaatca gaattggtta attggttgta acactggcag     300
agcattacgc tgacttgacg ggacggcggc tttgttgaat aaatcgaact tttgctgagt     360
tgaaggatct ccccgcgcgt tggccgattc attaatgcag ctggcacgac aggtttcccg     420
actggaaagc gggcagtgag cgcaacgcaa ttaatgtgag ttagctcact cattaggcac     480
cccaggcttt acactttatg cttccggctc gtatgttgtg tggaattgtg agcggataac     540
aatttcaagg agatatacat atgaacaata acgatctctt tcaggcatca cgtcggcgtt     600
ttctggcaca actcggcggc ttaaccgtcg ccgggatgct ggggccgtca ttgttaacgc     660
cgcgacgtgc gactgcgcat aatgggtgct ttgccaaggg taccaatgtt ttaatggcgg     720
atgggtctat tgaatgtatt gaaaacattg aggttggtaa taaggtcatg ggtaaagatg     780
gcagacctcg tgaggtaatt aaattgccca gaggaagaga aactatgtac agcgtcgttc     840
agaaaagtca gcacagagcc cacaaaagtg attcaagtcg tgaagtgcca gaattactca     900
agtttacgtg taatgcgacc catgagttgg ttgttagaac acctcgtagt gtccgccgtt     960
tgtctcgtac cattaagggt gtcgaatatt ttgaagttat tacttttgag atgggccaaa    1020
agaaagcccc cgacggtaga attgttgagc ttgtcaagga agtttcaaag agctacccaa    1080
tatctgaggg gcctgagaga gccaacgaat tagtagaatc ctatagaaag gcttcaaata    1140
aagcttattt tgagtggact attgaggcca gagatctttc tctgttgggt tcccatgttc    1200
gtaaagctac ctaccagact tacgcgccaa ttctttatga gaatgaccac ttttcgact     1260 acatgcaaaa aagtaagttt catctcacca ttgaaggtcc aaaagtactt gcttatttac    1320
ttggtttatg gattggtgat ggattgtctg acaggcgaac ttttcggtt gattccagag     1380 atacttcttt gatggaacgt gttactgaat atgctgaaaa gttgaatttg tgcgccgagt    1440
ataaggacag aaaagaacca caagttgcca aaactgttaa tttgtactct aaagttgtca    1500
gaggtaccat ggccggatcc gctgcccctc aacgcagaaa gagtatgaag atcgtggaag    1560
tcaaacaccc actcgtcaaa cacaagctgg gactgatgcg tgagcaagat atcagcacca    1620
```

```
agcgctttcg cgaactcgct tccgaagtgg gtagcctgct gacttacgaa gcgaccgccg   1680
acctcgaaac ggaaaaagta actatcgaag gctggaacgg cccggtagaa atcgaccaga   1740
tcaaaggtaa gaaaattacc gttgtgccaa ttctgcgtgc gggtcttggt atgatggacg   1800
gtgtgctgga aaacgttccg agcgcgcgca tcagcgttgt cggtatgtac cgtaatgaag   1860
aaacgctgga gccggtaccg tacttccaga aactggtttc taacatcgat gagcgtatgg   1920
cgctgatcgt tgacccaatg ctggcaaccg gtggttccgt tatcgcgacc atcgacctgc   1980
tgaaaaaagc gggctgcagc agcatcaaag ttctggtgct ggtagctgcg ccagaaggta   2040
tcgctgcgct ggaaaaagcg cacccggacg tcgaactgta taccgcatcg attgatcagg   2100
gactgaacga gcacgggata cattattccg ggcctcggcg atgccgggtc gaccatcatc   2160
atcatcatca ttgagtttaa acggtctcca gcttggctgt tttggcggat gagagaagat   2220
tttcagcctg atacagatta aatcagaacg cagaagcggt ctgataaaac agaatttgcc   2280
tggcggcagt agcgcggtgg tcccacctga ccccatgccg aactcagaag tgaaacgccg   2340
tagcgccgat ggtagtgtgg ggtctcccca tgcgagagta gggaactgcc aggcatcaaa   2400
taaaacgaaa ggctcagtcg aaagactggg cctttcgttt tatctgttgt ttgtcggtga   2460
acgatatctg cttttcttcg cgaattaatt ccgcttcgca acatgtgagc aaaaggccag   2520
caaaaggcca ggaaccgtaa aaaggccgcg ttgctggcgt ttttccatag gctccgcccc   2580
cctgacgagc atcacaaaaa tcgacgctca agtcagaggt ggcgaaaccc gacaggacta   2640
taaagatacc aggcgtttcc ccctggaagc tccctcgtgc gctctcctgt tccgaccctg   2700
ccgcttaccg gatacctgtc cgcctttctc ccttcgggaa gcgtggcgct ttctcatagc   2760
tcacgctgta ggtatctcag ttcggtgtag gtcgttcgct ccaagctggg ctgtgtgcac   2820
gaaccccccg ttcagcccga ccgctgcgcc ttatccggta actatcgtct gaatccaac    2880
ccggtaagac acgacttatc gccactggca gcagccactg gtaacaggat tagcagagcg   2940
aggtatgtag gcggtgctac agagttcttg aagtggtggc ctaactacgg ctacactaga   3000
aggacagtat ttggtatctg cgctctgctg aagccagtta ccttcggaaa aagagttggt   3060
agctcttgat ccggcaaaca aaccaccgct ggtagcggtg gtttttttgt ttgcaagcag   3120
cagattacgc gcagaaaaaa aggatctcaa gaagatcctt tgatcttttc tacgggtct    3180
gacgctcagt ggaacgaaaa ctcacgttaa gggattttgg tcatgagttg tgtctcaaaa   3240
tctctgatgt tacattgcac aagataaaaa tatatcatca tgaacaataa aactgtctgc   3300
ttacataaac agtaatacaa ggggtgttat gagccatatt caacgggaaa cgtcttgctc   3360
gaggccgcga ttaaattcca acatggatgc tgatttatat gggtataaat gggctcgcga   3420
taatgtcggg caatcaggtg cgacaatcta tcgattgtat gggaagcccg atgcgccaga   3480
gttgtttctg aaacatggca aaggtagcgt tgccaatgat gttacagatg agatggtcag   3540
actaaactgg ctgacggaat ttatgcctct tccgaccatc aagcatttta tccgtactcc   3600
tgatgatgca tggttactca ccactgcgat ccccgggaaa acagcattcc aggtattaga   3660
agaatatcct gattcaggtg aaaatattgt tgatgcgctg gcagtgttcc tgcgccggtt   3720
gcattcgatt cctgtttgta attgtccttt aacagcgat cgcgtatttc gtctagctca    3780
ggcgcaatca cgaatgaata acggtttggt tgatgcgagt gattttgatg acgagcgtaa   3840
tggctggcct gttgaacaag tctggaaaga atgcat                             3877
```

<210> SEQ ID NO 2

```
<211> LENGTH: 1459
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<221> NAME/KEY: modified_base
<222> LOCATION: (1361)..(1363)
<223> OTHER INFORMATION: a, c, t, g, unknown or other

<400> SEQUENCE: 2
gcggccgctg cactgggtat tcgcaataat cttaatactg agaatccatt atgggacgct      60
attgttggct taggattctt gaaggacggt gtcaaaaata ttccttcttt cttgtctacg     120
gacaatatcg gtactcgtga acatttctt gctggtctaa ttgattctga tggctatgtt     180
actgatgagc atggtattaa agcaacaata aagacaattc atacttctgt cagagatggt     240
ttggtttccc ttgctcgttc tttaggctta gtagtctcgg ttaacgcaga acctgctaag     300
gttgacatga atggcaccaa acataaaatt agttatgcta tttatatgtc tggtggagat     360
gttttgctta acgttctttc gaagtgtgcc ggctctaaaa aattcaggcc tgctcccgcc     420
gctgcttttg cacgtgagtg ccccggatttt tatttcgagt tacaagaatt gaaggaagac     480
gattattatg ggattacttt atctgatgat tctgatcatc agttttgct tgccaaccag     540 gttgtcgtcc ataattgcca cccagaaacg ctggtgaaag taaaagatgc tgaagatcag     600
ttgggtgcac gagtgggtta catcgaactg gatctcaaca gcggtaagat ccttgagagt     660
tttcgccccg aagaacgttt tccaatgatg agcacttta aagttctgct atgtggcgcg     720
gtattatccc gtgttgacgc cgggcaagag caactcggtc gccgcataca ctattctcag     780
aatgacttgg ttgagtactc accagtcaca gaaaagcatc ttacgatgg catgacagta     840 agagaattat gcagtgctgc cataaccatg agtgataaca ctgcggccaa cttacttctg     900
acaacgatcg gaggaccgaa ggagctaacc gcttttttgc acaacatggg ggatcatgta     960
actcgccttg atcgttggga accggagctg aatgaagcca taccaaacga cgagcgtgac    1020
accacgatgc ctgtagcaat ggcaacaacg ttgcgcaaac tattaactgg cgaactactt    1080
actctagctt cccggcaaca attaatagac tggatggagg cggataaagt tgcaggacca    1140
cttctgcgct cggcccttcc ggctggctgg tttattgctg ataaatctgg agccggtgag    1200
cgtgggtctc gcggtatcat tgcagcactg gggccagatg gtaagccctc ccgtatcgta    1260
gttatctaca cgacggggag tcaggcaact atggatgaac gaaatagaca gatcgctgag    1320
ataggtgcct cactgattaa gcattggtaa gagtcagacc nnntttactc atataaccttt    1380 tactccggcg gccatggata tcggactagg tacctgacct aaggtattcg gaagaattca    1440
ctgattctcc ggcggccgc                                                  1459

<210> SEQ ID NO 3
<211> LENGTH: 1582
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<221> NAME/KEY: modified_base
<222> LOCATION: (1484)..(1486)
<223> OTHER INFORMATION: a, c, t, g, unknown or other

<400> SEQUENCE: 3
aaagcggccg ctgcactgaa agacgcgcag actaattcga gctcgaacaa caacaacaat      60
```

```
aacaataaca acaacctcgg gatcgaggga aggatttcag aattcgccct cgcagagggc      120
actcggatct tcgatccggt caccggtaca acgcatcgca tcgaggatgt tgtcggtggg      180
cgcaagccta ttcatgtcgt ggctgctgcc aaggacggaa cgctgcatgc gcggcccgtg      240
gtgtcctggt tcgaccaggg aacgcgggat gtgatcgggt tgcggatcgc cggtggcgcc      300
atcctgtggg cgacacccga tcacaaggtg ctgacagagt acggctggcg tgccgccggg      360
gaactccgca agggagacag ggtggcgcaa ccgcgacgct tcgatggatt cggtgacagt      420
gcgccgattc cggcgcgcgt gcaggcgctc gcggatgccc tggatgacaa attcctgcac      480
gacatgctgg cggaagaact ccgctattcc gtgatccgag aagtgctgcc aacgcggcgg      540
gcacgaacgt tcggcctcga ggtcgaggaa ctgcacaccc tcgtcgccga aggggttgtt      600
gtacacaact gtatgaaaca ataccaagat ttaattaaag acattttga aaatggttat       660 gaaaccgatg atcgtacagg cacaggaaca attgctctgt tcggatctaa attacgctgg      720
gatttaacta aaggttttcc tgcggtaaca actaagaagc tcgcctggaa agcttgcatt      780
gctgagctaa tatggttttt atcaggaagc acaaatgtca atgatttacg attaattcaa      840
cacgattcgt taatccaagg caaaacagtc tgggatgaaa attacgaaaa tcaagcaaaa      900
gatttaggat accatagcgg tgaacttggt ccaatttatg gaaaacagtg gcgtgatttt      960
ggtggtgtag accaaattat agaagttatt gatcgtatta aaaaactgcc aaatgatagg     1020
cgtcaaattg tttctgcatg gaatccagct gaacttaaat atatggcatt accgccttgt     1080
catatgttct atcagtttaa tgtgcgtaat ggctatttgg atttgcagtg gtatcaacgc     1140
tcagtagatg ttttcttggg tctaccgttt aatattgcgt catatgctac gttagttcat     1200
attgtagcta agatgtgtaa tcttattcca ggggatttga tattttctgg tggtaatact     1260
catatctata tgaatcacgt agaacaatgt aaagaaattt tgaggcgtga acctaaagag     1320
ctttgtgagc tggtaataag tggtctacct tataaattcc gatatctttc tactaaagaa     1380
caattaaaat atgttcttaa acttaggcct aaagatttcg ttcttaacaa ctatgtatca     1440
caccctccta ttaaaggaaa gatggcggtg taagagtcag accnnnttta ctcatataac     1500
ctttactccg gcggccatgg atatcggact aggtacctga cctaaggtat tcggaagaat     1560
tcactgattc tccggcggcc gc                                              1582
```

<210> SEQ ID NO 4
<211> LENGTH: 19
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 4

```
agatctgact cggcgcacg                                                     19
```

<210> SEQ ID NO 5
<211> LENGTH: 14
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 5

```
cgtgcgccga gtca                                                          14
```

```
<210> SEQ ID NO 6
<211> LENGTH: 11
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (1)..(5)
<223> OTHER INFORMATION: a, c, t, g, unknown or other

<400> SEQUENCE: 6
nnnnntgact c                                                           11

<210> SEQ ID NO 7
<211> LENGTH: 11
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (7)..(11)
<223> OTHER INFORMATION: a, c, t, g, unknown or other

<400> SEQUENCE: 7
gagtcannnn n                                                           11

<210> SEQ ID NO 8
<211> LENGTH: 13
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 8
tagagatcga ctc                                                         13

<210> SEQ ID NO 9
<211> LENGTH: 10
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 9
gagtcagatc                                                             10

<210> SEQ ID NO 10
<211> LENGTH: 14
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (1)..(1)
<223> OTHER INFORMATION: a, c, t, g, unknown or other

<400> SEQUENCE: 10
ntagagatcg actc                                                        14

<210> SEQ ID NO 11
```

```
<211> LENGTH: 11
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (11)..(11)
<223> OTHER INFORMATION: a, c, t, g, unknown or other

<400> SEQUENCE: 11
gagtcagatc n                                                          11

<210> SEQ ID NO 12
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 12
agatcgactc ggagtatt                                                   18

<210> SEQ ID NO 13
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 13
taaaggagtc agatctag                                                   18

<210> SEQ ID NO 14
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 14
agatcgcgag cggcgcac                                                   18

<210> SEQ ID NO 15
<211> LENGTH: 19
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 15
agatctgaag cggcgcacg                                                  19

<210> SEQ ID NO 16
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (1)..(5)
<223> OTHER INFORMATION: a, c, t, g, unknown or other
```

```
<400> SEQUENCE: 16
nnnnngcgag cggcgcacga aaaa                                              24

<210> SEQ ID NO 17
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (15)..(24)
<223> OTHER INFORMATION: a, c, t, g, unknown or other

<400> SEQUENCE: 17
cgtgcgccgc ttcannnnnn nnnn                                              24

<210> SEQ ID NO 18
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (15)..(24)
<223> OTHER INFORMATION: a, c, t, g, unknown or other

<400> SEQUENCE: 18
gtgcagccgc ttcannnnnn nnnn                                              24

<210> SEQ ID NO 19
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (1)..(5)
<223> OTHER INFORMATION: a, c, t, g, unknown or other

<400> SEQUENCE: 19
nnnnngcgag cggcgcacga aaaactgcac                                        30

<210> SEQ ID NO 20
<211> LENGTH: 10
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (1)..(5)
<223> OTHER INFORMATION: a, c, t, g, unknown or other

<400> SEQUENCE: 20 nnnnntagag                                                              10

<210> SEQ ID NO 21
<211> LENGTH: 20
<212> TYPE: DNA
<213> ORGANISM: Artificial Sequence
<220> FEATURE:
```

```
<223> OTHER INFORMATION: Description of Artificial Sequence: Synthetic
      oligonucleotide

<400> SEQUENCE: 21
agatctgcgg ccgccgcacg                                              20

<210> SEQ ID NO 22
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 22
agatggcgcg cccgcacg                                                18

<210> SEQ ID NO 23
<211> LENGTH: 14
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (1)..(5)
<223> OTHER INFORMATION: a, c, t, g, unknown or other

<400> SEQUENCE: 23
nnnnntggcg cgcc                                                    14

<210> SEQ ID NO 24
<211> LENGTH: 14
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (10)..(14)
<223> OTHER INFORMATION: a, c, t, g, unknown or other

<400> SEQUENCE: 24
ggcgcgccan nnnn                                                    14

<210> SEQ ID NO 25
<211> LENGTH: 12
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (8)..(12)
<223> OTHER INFORMATION: a, c, t, g, unknown or other

<400> SEQUENCE: 25
ggccgcannn nn                                                      12

<210> SEQ ID NO 26
<211> LENGTH: 13
<212> TYPE: DNA
<213> ORGANISM: Artificial Sequence
<220> FEATURE:
<223> OTHER INFORMATION: Description of Artificial Sequence: Synthetic
      oligonucleotide
```

<400> SEQUENCE: 26
gcggccgctg cac                                                              13

<210> SEQ ID NO 27
<211> LENGTH: 44
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 27
gagtcagacc tagtttactc atataacctt tactccggcg cgcc                            44

<210> SEQ ID NO 28
<211> LENGTH: 22
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (1)..(8)
<223> OTHER INFORMATION: a, c, t, g, unknown or other

<400> SEQUENCE: 28
nnnnnnnntg cggccgctgc ac                                                    22

<210> SEQ ID NO 29
<211> LENGTH: 50
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (46)..(50)
<223> OTHER INFORMATION: a, c, t, g, unknown or other

<400> SEQUENCE: 29
gagtcagacc tagtttactc atataacctt tactccggcg cgcctnnnnn                      50

<210> SEQ ID NO 30
<211> LENGTH: 41
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (1)..(1)
<223> OTHER INFORMATION: a, c, t, g, unknown or other
<220> FEATURE:
<221> NAME/KEY: modified_base
<222> LOCATION: (37)..(41)
<223> OTHER INFORMATION: a, c, t, g, unknown or other

<400> SEQUENCE: 30
ntagtttact catataacct ttactccggc gcgcctnnnn n                               41

<210> SEQ ID NO 31
<211> LENGTH: 109
<212> TYPE: DNA
<213> ORGANISM: Artificial Sequence
<220> FEATURE:

```
<223> OTHER INFORMATION: Description of Artificial Sequence: Synthetic
      polynucleotide
<220> FEATURE:
<221> NAME/KEY: modified_base
<222> LOCATION: (6)..(10)
<223> OTHER INFORMATION: a, c, t, g, unknown or other
<220> FEATURE:
<221> NAME/KEY: modified_base
<222> LOCATION: (14)..(25)
<223> OTHER INFORMATION: a, c, t, g, unknown or other
<220> FEATURE:
<221> NAME/KEY: modified_base
<222> LOCATION: (28)..(32)
<223> OTHER INFORMATION: a, c, t, g, unknown or other
<220> FEATURE:
<221> NAME/KEY: modified_base
<222> LOCATION: (37)..(89)
<223> OTHER INFORMATION: a, c, t, g, unknown or other
<220> FEATURE:
<221> NAME/KEY: modified_base
<222> LOCATION: (92)..(96)
<223> OTHER INFORMATION: a, c, t, g, unknown or other

<400> SEQUENCE: 31
gagtcnnnnn gcgnnnnnnn nnnnacnnn nnctccnnnn nnnnnnnnnn nnnnnnnnnn    60
nnnnnnnnnn nnnnnnnnnn nnnnnnnnna cnnnnnctcc ggcggccgc                109

<210> SEQ ID NO 32
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Any amino acid

<400> SEQUENCE: 32

Xaa Glu Leu Gly Leu Glu Phe Pro Asn Leu Pro Tyr Tyr Ile Asp Gly
1               5                   10                  15

Asp Val Lys Lys
            20

<210> SEQ ID NO 33
<211> LENGTH: 6
<212> TYPE: PRT
<213> ORGANISM: Artificial Sequence
<220> FEATURE:
<223> OTHER INFORMATION: Description of Artificial Sequence: Synthetic
      6xHis tag

<400> SEQUENCE: 33

His His His His His His
1               5

<210> SEQ ID NO 34
<211> LENGTH: 13
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 34
gagtcgatct cta                                                       13

<210> SEQ ID NO 35
```

```
<211> LENGTH: 10
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 35
gatctgactc                                                               10

<210> SEQ ID NO 36
<211> LENGTH: 14
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (14)..(14)
<223> OTHER INFORMATION: a, c, t, g, unknown or other

<400> SEQUENCE: 36
gagtcgatct ctan                                                          14

<210> SEQ ID NO 37
<211> LENGTH: 11
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (1)..(1)
<223> OTHER INFORMATION: a, c, t, g, unknown or other

<400> SEQUENCE: 37
ngatctgact c                                                             11

<210> SEQ ID NO 38
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 38
aatactccga gtcgatct                                                      18

<210> SEQ ID NO 39
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 39
ctagatctga ctccttta                                                      18

<210> SEQ ID NO 40
<211> LENGTH: 13
<212> TYPE: DNA
<213> ORGANISM: Artificial Sequence
<220> FEATURE:
<223> OTHER INFORMATION: Description of Artificial Sequence: Synthetic
      oligonucleotide
```

-continued

<400> SEQUENCE: 40
gtgcgccgct cgc                                                        13

<210> SEQ ID NO 41
<211> LENGTH: 14
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 41
acttcgccgc gtgc                                                       14

<210> SEQ ID NO 42
<211> LENGTH: 25
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (21)..(25)
<223> OTHER INFORMATION: a, c, t, g, unknown or other

<400> SEQUENCE: 42 tttttcgtg cgccgctcgc nnnnn                                            25

<210> SEQ ID NO 43
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (1)..(10)
<223> OTHER INFORMATION: a, c, t, g, unknown or other

<400> SEQUENCE: 43
nnnnnnnnnn tgaagcggcg cacg                                            24

<210> SEQ ID NO 44
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (1)..(10)
<223> OTHER INFORMATION: a, c, t, g, unknown or other

<400> SEQUENCE: 44
nnnnnnnnnn tgaagcgggt gcac                                            24

<210> SEQ ID NO 45
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base

```
<222> LOCATION: (26)..(30)
<223> OTHER INFORMATION: a, c, t, g, unknown or other

<400> SEQUENCE: 45
gtgcagtttt tcgtgcgccg ctcgcnnnnn                                30

<210> SEQ ID NO 46
<211> LENGTH: 15
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 46
cgtgcggcgg ccgca                                                15

<210> SEQ ID NO 47
<211> LENGTH: 15
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 47
cgtgcgggcg cgcca                                                15

<210> SEQ ID NO 48
<211> LENGTH: 13
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 48
gtgcagcggc cgc                                                  13

<210> SEQ ID NO 49
<211> LENGTH: 44
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 49
ggcgcgccgg agtaaaggtt atatgagtaa actagatctg actc                44

<210> SEQ ID NO 50
<211> LENGTH: 22
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (15)..(22)
<223> OTHER INFORMATION: a, c, t, g, unknown or other

<400> SEQUENCE: 50
gtgcagcggc cgcannnnnn nn                                        22

<210> SEQ ID NO 51
<211> LENGTH: 50
```

```
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (1)..(5)
<223> OTHER INFORMATION: a, c, t, g, unknown or other

<400> SEQUENCE: 51
nnnnnaggcg cgccggagta aaggttatat gagtaaacta gatctgactc            50

<210> SEQ ID NO 52
<211> LENGTH: 41
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (1)..(5)
<223> OTHER INFORMATION: a, c, t, g, unknown or other
<220> FEATURE:
<221> NAME/KEY: modified_base
<222> LOCATION: (41)..(41)
<223> OTHER INFORMATION: a, c, t, g, unknown or other

<400> SEQUENCE: 52
nnnnnaggcg cgccggagta aaggttatat gagtaaacta n                     41

<210> SEQ ID NO 53
<211> LENGTH: 109
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<221> NAME/KEY: modified_base
<222> LOCATION: (14)..(18)
<223> OTHER INFORMATION: a, c, t, g, unknown or other
<220> FEATURE:
<221> NAME/KEY: modified_base
<222> LOCATION: (21)..(73)
<223> OTHER INFORMATION: a, c, t, g, unknown or other
<220> FEATURE:
<221> NAME/KEY: modified_base
<222> LOCATION: (78)..(82)
<223> OTHER INFORMATION: a, c, t, g, unknown or other
<220> FEATURE:
<221> NAME/KEY: modified_base
<222> LOCATION: (85)..(96)
<223> OTHER INFORMATION: a, c, t, g, unknown or other
<220> FEATURE:
<221> NAME/KEY: modified_base
<222> LOCATION: (100)..(104)
<223> OTHER INFORMATION: a, c, t, g, unknown or other

<400> SEQUENCE: 53
gcggccgccg gagnnnnngt nnnnnnnnnn nnnnnnnnnn nnnnnnnnnn nnnnnnnnnn   60
nnnnnnnnnn nnnggagnnn nnctnnnnnn nnnnnncgcn nnnngactc             109
```